(12) United States Patent
Miranda et al.

(10) Patent No.: US 10,690,766 B2
(45) Date of Patent: Jun. 23, 2020

(54) BIOMETRIC AUTHENTICATION USING WIDEBAND UHF/VHF RADAR

(71) Applicant: Government of the United States, as represented by the Secretary of the Air Force, Wright-Patterson AFB, OH (US)

(72) Inventors: Analee M Miranda, Troy, NY (US); Loria L Wang, Beavercreek, OH (US); Stephanie R Keith, Charlottesvulle, VA (US)

(73) Assignee: Government of the United States, as represented by the Secretary of the Air Force, Washington, DC (US)

( * ) Notice: Subject to any disclaimer, the term of this patent is extended or adjusted under 35 U.S.C. 154(b) by 130 days.

(21) Appl. No.: 15/913,335

(22) Filed: Mar. 6, 2018

(65) Prior Publication Data

US 2018/0252806 A1    Sep. 6, 2018

Related U.S. Application Data

(60) Provisional application No. 62/467,274, filed on Mar. 6, 2017, provisional application No. 62/467,277, filed on Mar. 6, 2017.

(51) Int. Cl.
*G01S 13/89* (2006.01)
*A61B 5/107* (2006.01)
(Continued)

(52) U.S. Cl.
CPC ............ *G01S 13/89* (2013.01); *A61B 5/1075* (2013.01); *A61B 5/4504* (2013.01);
(Continued)

(58) Field of Classification Search
CPC ........ G01S 13/89; G01S 7/412; G01S 7/2813; G01S 13/0209; G01S 2007/2886;
(Continued)

(56) References Cited

U.S. PATENT DOCUMENTS 5,329,286 A * 7/1994 Lammers ............... G01S 7/4052
                                                        342/165
5,557,283 A    9/1996 Sheen et al.
(Continued)

OTHER PUBLICATIONS

Wang, L. et al., "A comparison of theoretical, computational, and experimental human electromagnetic scattering at VHF and UHF," NAECON 2014—IEEE National Aerospace and Electronics Conference, Dayton, OH, 2014, pp. 95-102.
(Continued)

*Primary Examiner* — Xuemei G Chen
(74) *Attorney, Agent, or Firm* — AFMCLO/JAZ; Charles R. Figer, Jr.

(57) ABSTRACT

A wideband RADAR system and method is provided for biometric identification and authentication of a human subject. The system includes a source of wideband RADAR signals, an amplifier, and a splitter in electrical communication with the source of wideband RADAR signals and configures to split a generated signal into a transmit signal and a reference transmit signal. A transmitting antenna is configured to transmit the transmit signal from the splitter toward a turntable configured to rotate the human subject. A receiving antenna is configured to receive transmitted signals reflected from the human subject. A controller is configured to process the received reflected signals and generate polar representations of biometric radar signature features to compare against known signatures of human subjects.

12 Claims, 21 Drawing Sheets

(51) Int. Cl.
| | |
|---|---|
| *G01S 7/28* | (2006.01) |
| *A61B 5/00* | (2006.01) |
| *G06K 9/00* | (2006.01) |
| *G01S 7/41* | (2006.01) |
| *G01S 13/02* | (2006.01) |
| *G01S 7/288* | (2006.01) |
| *A61B 5/18* | (2006.01) |

(52) U.S. Cl.
CPC ............ *G01S 7/2813* (2013.01); *G01S 7/412* (2013.01); *G01S 13/0209* (2013.01); *G06K 9/00369* (2013.01); *A61B 5/18* (2013.01); *G01S 7/414* (2013.01); *G01S 2007/2886* (2013.01)

(58) Field of Classification Search
CPC ... G01S 7/414; G06K 9/00369; A61B 5/4504; A61B 5/1075; A61B 5/18; A61B 5/1171
See application file for complete search history.

(56) References Cited

U.S. PATENT DOCUMENTS

| | | | | |
|---|---|---|---|---|
| 5,867,121 | A * | 2/1999 | Erickson | G01S 7/062 342/185 |
| 7,009,552 | B2 * | 3/2006 | Sako | G01S 13/32 342/118 |
| 7,537,181 | B2 * | 5/2009 | Owens | F41G 7/226 244/3.1 |
| 7,692,576 | B2 * | 4/2010 | Mainds | G01S 7/298 342/176 |
| 7,916,068 | B2 * | 3/2011 | Wicks | G01S 13/5248 342/109 |
| 8,026,840 | B2 | 9/2011 | Dwelly et al. | |
| 8,049,659 | B1 * | 11/2011 | Sullivan | F41G 3/14 342/90 |
| 8,232,866 | B2 | 7/2012 | McGrath et al. | |
| 9,383,426 | B2 * | 7/2016 | Mohamadi | G01S 7/415 |
| 9,442,189 | B2 * | 9/2016 | Wang | G01S 13/0209 |
| 9,759,810 | B1 * | 9/2017 | Sankar | G01S 7/282 |
| 2008/0074307 | A1 * | 3/2008 | Boric-Lubecke | A61B 5/0205 342/28 |
| 2008/0074312 | A1 * | 3/2008 | Cross | G06T 17/05 342/25 A |
| 2008/0234899 | A1 * | 9/2008 | Breed | B60N 2/002 701/47 |
| 2009/0015460 | A1 * | 1/2009 | Fox | G01S 7/2922 342/53 |
| 2009/0146865 | A1 * | 6/2009 | Watanabe | G01S 13/50 342/27 |
| 2009/0295623 | A1 * | 12/2009 | Falk | G01S 7/023 342/109 |
| 2010/0145166 | A1 * | 6/2010 | Pickler | A61B 5/16 600/301 |
| 2010/0152600 | A1 * | 6/2010 | Droitcour | A61B 5/05 600/534 |
| 2012/0200453 | A1 * | 8/2012 | Brosche | G01S 7/288 342/175 |
| 2014/0336515 | A1 * | 11/2014 | Tangy | A61B 5/015 600/474 |
| 2015/0301167 | A1 * | 10/2015 | Sentelle | A61B 5/0205 342/22 |
| 2016/0048672 | A1 * | 2/2016 | Lux | G06F 21/32 340/5.82 |
| 2016/0213303 | A1 * | 7/2016 | Hyde | A61B 5/1113 |
| 2016/0359569 | A1 * | 12/2016 | Dailey | H04B 10/90 |
| 2017/0322297 | A1 * | 11/2017 | Dai | G01S 7/04 |
| 2018/0083720 | A1 * | 3/2018 | Kollmann | H04B 17/13 |
| 2018/0106889 | A1 * | 4/2018 | Schuck | F41G 5/08 |
| 2018/0157330 | A1 * | 6/2018 | Gu | G01S 7/415 |
| 2018/0180728 | A1 * | 6/2018 | Shamain | A61B 5/0507 |
| 2018/0263502 | A1 * | 9/2018 | Lin | A61B 8/5223 |

OTHER PUBLICATIONS

Keith, Stephanie R., "Thesis: Discrimination Between Child and Adult Forms Using Radar Frequency Signature Analysis," Air Force Institute of Technlogy, AFIT-ENP-13-M-20, Mar. 14, 2013.
Wildes, Richard P., "Iris Recognition: An Emerging Biometric Technology," Proceedings of the IEEE, vol. 85, No. 9, pp. 1348-1363, Sep. 1997.

* cited by examiner

| FREQUENCY RANGE (MHz) | MAXIMUM POWER DENSITY (S) (Mw/cm²) | AVERAGE TIME (MINUTES) |
|---|---|---|
| 0.3 - 3.0 | (100)* | 6 |
| 3.0 - 30 | (900/$f^2$)* | 6 |
| 30 - 300 | 1 | 6 |
| 300 - 1500 | f/300 | 6 |
| 1500 - 100000 | 5.0 | 6 |

| FREQUENCY RANGE (MHz) | MAXIMUM POWER DENSITY (S) (Mw/cm²) | AVERAGE TIME (MINUTES) |
|---|---|---|
| 0.3 – 3.0 | (100)* | 30 |
| 3.0 – 30 | $(900/f^2)$* | 20 |
| 30 – 300 | 0.1 | 30 |
| 300 – 1500 | f/1500 | 30 |
| 1500 – 100000 | 1.0 | 30 |

FIRST DERIVATIVE

B=MAX

A=MIN

SCALE BETWEEN MINIMUM
AND MAXIMUM $B' - A' = N'/8$ $A', A'+N'/8, ..., B'$

↓   ↓    ↓   ↓

0   1   ... 7

SECOND DERIVATIVE

B=MAX

A=MIN

SCALE BETWEEN MINIMUM
AND MAXIMUM $B'' - A'' = N''/8$ $A'', A''+N''/8, ..., B''$

↓   ↓    ↓   ↓

0   1   ... 7

| Algorithm 1.0: Preprocessing Algorithm |
|---|
| Input: The current measurement vector ($v_c$) |
| Output: Preprocessed measurement data ($v_p$) |
| Step 1: The system noise distribution ($y$) is determined several times each day.<br><br>Step 2: The data is centered by matching the template measurement vector's ($v_{c_t}$) antenna response to the current raw measurement vector's ($v_c$) antenna response via a shift function. The centered measurement vector is now $v_{cc}$.<br><br>Step 3: Subtract the noise distribution from $v_{cc}$ and $v_{c_t c_t}$. The centered background-subtracted measurement vector is now $v_{ccb}$.<br><br>Step 4: Remove the highest peak (antenna response) via simple filter based on the antenna response index (location). For example, a simple-filter can be denoted by<br><br>$$[1\ 1\ 1\ 1\ 1\ 1\ 0.001\ 1\ 1\ 1]^T$$<br><br>where T denotes a transpose. The output is $v_p$. |

*FIG. 27A*

| Algorithm 1.1: Signal Conditioning Algorithm |
|---|
| Input: The preprocessed measurement vector ($v_p$) |
| Output: The peak measurement vector ($P_k$) |
| Step 1: Perform first and second numerical derivative tests on $v_p$ via shift functions.<br><br>Step 2: An average value filter ($F_a$) based on the mean value theory is used to determine the peak locations.<br><br>Step 3: The peak measurement vector ($P_k$) is determined by multiplying $F_a$ by $v_p$. |

*FIG. 27B*

| |
|---|
| *Algorithm 1.2:* Comparison Algorithm |
| Input: The current peak vector ($P_k$) |
| Output: Biometric authentication initial decision $D \in [0,1]$ |
| Step 1: Determine the number of peaks ($p$) in $P_k$.<br><br>Step 2: Determine $D_c$ and $D$ via $$D_c = \|P_k \cap P_{k'}\| + 0.5\,(p + p') + |\overline{P_k} - \overline{P_{k'}}|$$ $$D = \frac{D_c}{\|D_c\|}$$ |

*FIG. 27C*

BIOMETRIC AUTHENTICATION USING WIDEBAND UHF/VHF RADAR

CROSS-REFERENCE TO RELATED APPLICATIONS

This application claims the benefit of and priority to U.S. Provisional Application Ser. No. 62/467,274, entitled "Biometric Signatures from Radar Scattering," filed on Mar. 6, 2017, and U.S. Provisional Application Ser. No. 62/467,277, entitled "Biometric Signatures from Radar Scattering," filed on Mar. 6, 2017, the entireties of which is incorporated by reference herein.

RIGHTS OF THE GOVERNMENT

The invention described herein may be manufactured and used by or for the Government of the United States for all governmental purposes without the payment of any royalty.

BACKGROUND OF THE INVENTION

Field of the Invention

The present invention generally relates to biometric authentication and, more particularly, biometric authentication by RADAR analysis of biometric markers.

Description of the Related Art

Contemporary forms of personal identification include use of biometric markers such as fingerprint, handwriting, human iris, and human retina analysis. As time progresses, however, technological advances render these personal identification and authentication methods less and less reliable due to advancing forgery techniques.

In contrast, a biometric marker analysis based on human bone pattern, size and shape is of great interest. Each individual has their own unique skeletal structure, which is composed of approximately 300 bones at birth that solidify to 206 bones at adulthood. Bone density generally reaches its apex at age 30 and is also stable for many years. Certain bone size ratios stabilize at age 10 and only slightly change with time, with skull size and features being the most stable and unique. Thus, an individual's skeletal structure is temporally invariant after a certain age.

RADAR is a technology that uses electromagnetic radiation in the radio frequency spectrum. Low-power RADAR uses a low-risk form of electromagnetic radiation that is used all over the world for communication, weather prediction, geo-location, and many other useful applications. Electromagnetic radiation scatters according to the well-known Maxwell's equations from Physics and has certain properties that make it attractive for use in personal identification, including its relative safety.

Contemporary technology, such as airport millimeter wave scanners that detect concealed weapons under the clothing of aircraft passengers, simply takes a near-surface image of the human body. But, the radiation wavelength is too small and the RADAR is not, in safe ranges, powerful enough to penetrate deeply into fat, muscle, and tissue to reach and scatter from the skeletal system. For this reason, millimeter wave technology cannot be reliably used for biometric authentication.

In contrast, standard X-ray, CT, and other similar medical technology can penetrate fat, muscle, and tissue to produce high-resolution images of a human skeleton. Unfortunately, some of these technologies use very powerful ionizing electromagnetic radiation that have large spectral power density, which in turn have higher associated safety risks and thus cannot be used on an ongoing basis. Some other contemporary research involves development of personal identification systems based on electromagnetic bone scattering analysis in the X-ray, Gamma ray, or Terahertz regimes. Unfortunately, again, safety concerns typically stunt progress in this area.

Other contemporary methods use micro-Doppler techniques to detect human heartbeat and activity. These methods only propose to biometrically identify individuals by their gait and heartbeat. These features may be extracted using well-known signal processing techniques, but have only been tested on a limited number of human volunteers. Although the techniques show promise, there is not sufficient evidence to guarantee that the motion signatures collected are unique. The most promising of the methods collect human heart beat signatures. Although it is well known that heart beat signatures are unique to an individual, the algorithms may be easily fooled by activity of a person and the physical fitness or health of an individual. Additionally, there are too many variables that can change a heartbeat signature; thus, the biometric signatures are time-variant and not necessarily a good candidate for identification.

Accordingly, there is a need in the art for safe biometric marker analysis techniques and methods to be used for personal identification and authentication.

SUMMARY OF THE INVENTION

The broad objective of the present invention is to provide a system for automatically identifying persons based on a stationary and micro-Doppler radar scattering (I/Q) and associated unique resonant scattering frequencies in the UHF/VHF regime. Further objectives of the invention include the ability to provide a radar-based biometric personal identification system for extremely reliable and rapid identification of a person; to provide a radar-based biometric personal identification system that can calculate the confidence level for any identification decision using a mathematically precise and rigorous measure of performance; and to provide a radar-based biometric personal identification system that provides identification of a person using very low spectral power density, among others.

Embodiments of the invention address the need in the art by providing a wideband RADAR system for biometric identification and authentication of a human subject. The RADAR system includes a source of wideband RADAR signals, an amplifier, and a splitter in electrical communication with the source of wideband RADAR signals, which is configure to split a generated signal into a transmit signal and a reference transmit signal. A transmitting antenna is configured to transmit the transmit signal from the splitter. A turntable is configured to rotate the human subject about a central access in order to generate RADAR signals from the human subject at different orientations. A receiving antenna is configured to receive the transmitted signals that are reflected from the human subject. Finally, a controller in the system is configured to process the received reflected signals and generate polar representations of biometric radar signature features to be used to compare against known signatures for identification and authentication.

Embodiments of the invention further provide a method of biometric identification and authentication of a human subject from wideband RADAR. I/Q wideband RADAR data is received, pre-processes, conditioned and then compared to a known signature. In the preprocessing step, the received data is centered and then noise is removed from the received data. Other background and unwanted signal is also removed from the received data. The preprocessed received data is then processed by initially performing first and second numerical derivative tests. Peak locations are determined and then a peak measurement vector is determined. The known signatures are retrieved from a library of saved subject templates.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

FIGS. 27A-27C contain representative algorithms for processing the RADAR data.

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION OF THE INVENTION

In contrast to the contemporary methods referenced above, RADAR technologies in the UHF and VHF regime have wavelengths that are capable of deeply penetrating the body, to access the skeletal regions and micro-Doppler features, without needing large spectral power densities. Unfortunately, radar images in these frequencies are often low-resolution and have longer processing times so many scientists neglect UHF-based RADAR imaging of humans for personal identification. However, embodiments of the invention utilize radar sensing in the UHF/VHF part of the spectrum. The embodiments, however, do not rely primarily on imaging. Instead, the embodiments rely on dosimetry-based signal processing techniques on specific features of I/Q data collected from a chamber that is calibrated for the specific purpose of human biometric identification.

Embodiments of the invention provide a new and unique method for authenticating personal identification with a very low likelihood of fraudulent manipulation. These embodiments use basic electromagnetic theory and precise mathematical theories coupled with advanced RADAR technology that accurately measures electromagnetic scattering in a secure anechoic chamber. In these embodiments, a specific combination of RADAR technology, RADAR frequencies, and known biological traits are utilized to determine a precise set of biometric indices specific to a unique individual that may be compared with others.

Figures 1, 2A:
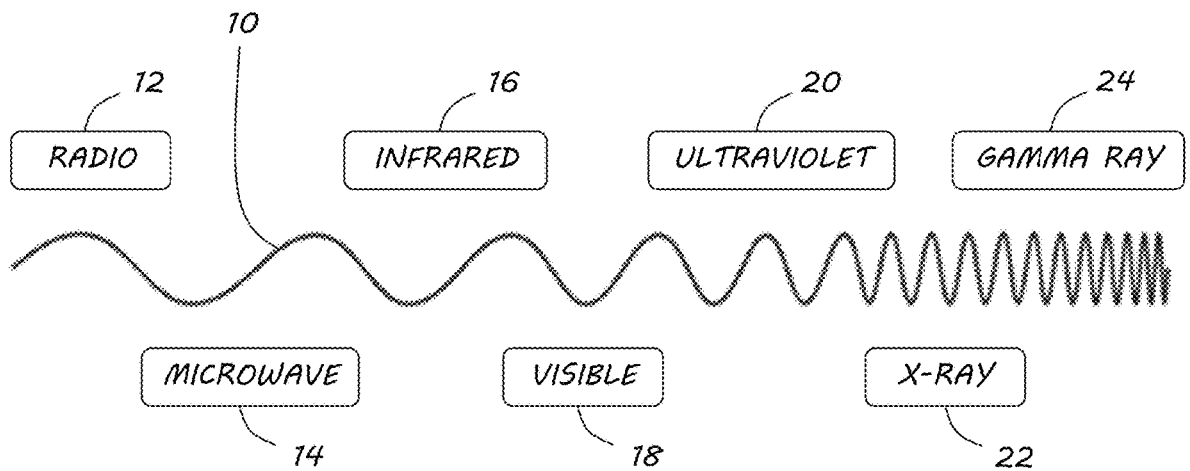
FIG. 1 is an illustration of an electromagnetic spectrum.
FIGS. 2A and 2B contain tables illustrating limits for maximum permissible exposure.
Figures 2B, 3:
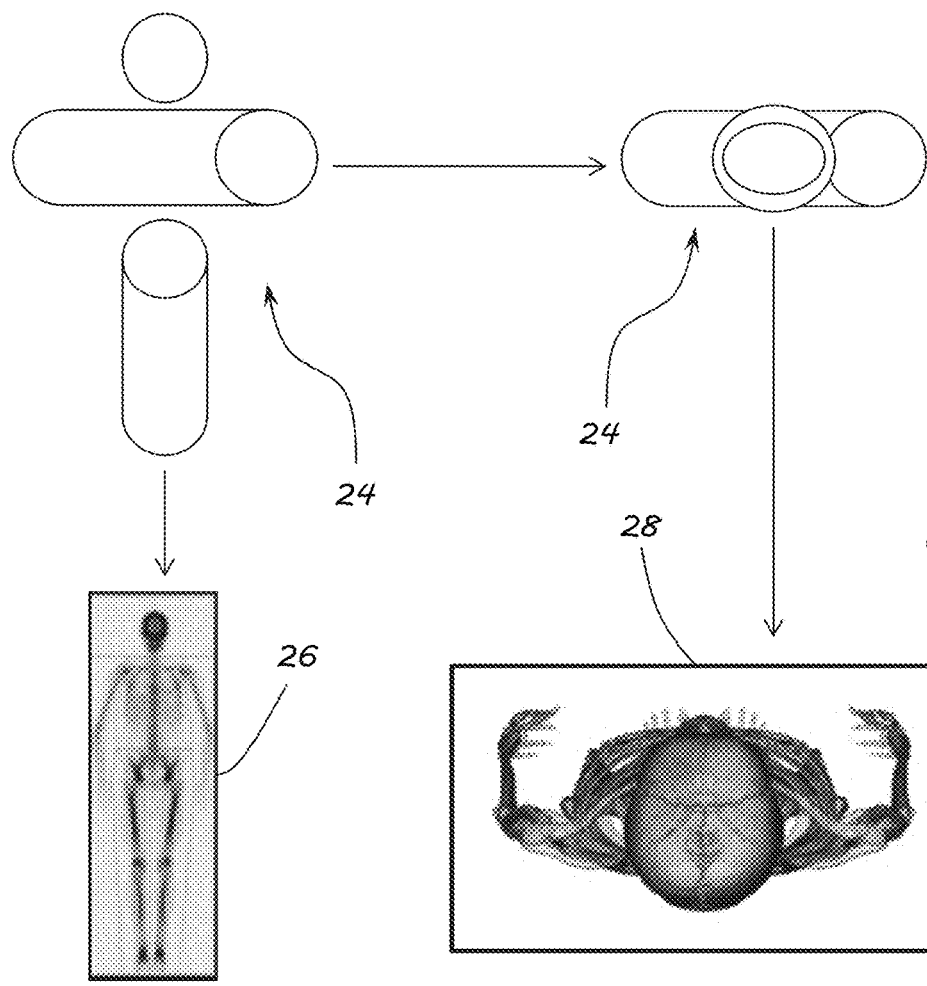
FIG. 3 is an illustration of a model for determining scattering characteristics vs. a human view.
Figure 4A:
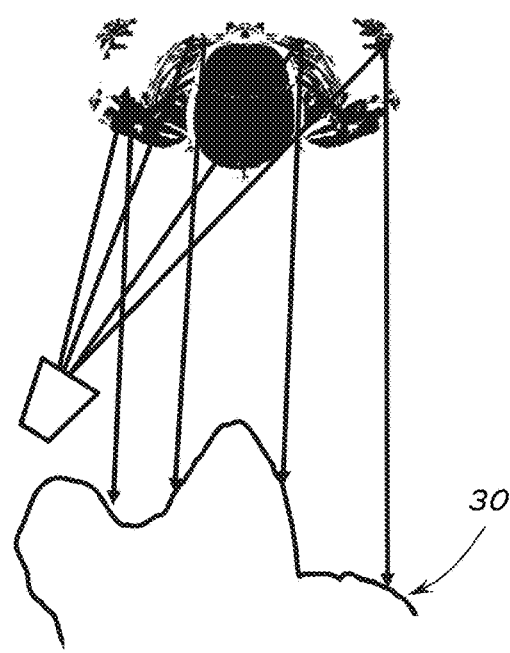
FIGS. 4A-4D are representations of a generation of a polar plot representation a RADAR signature.
Figure 4B:
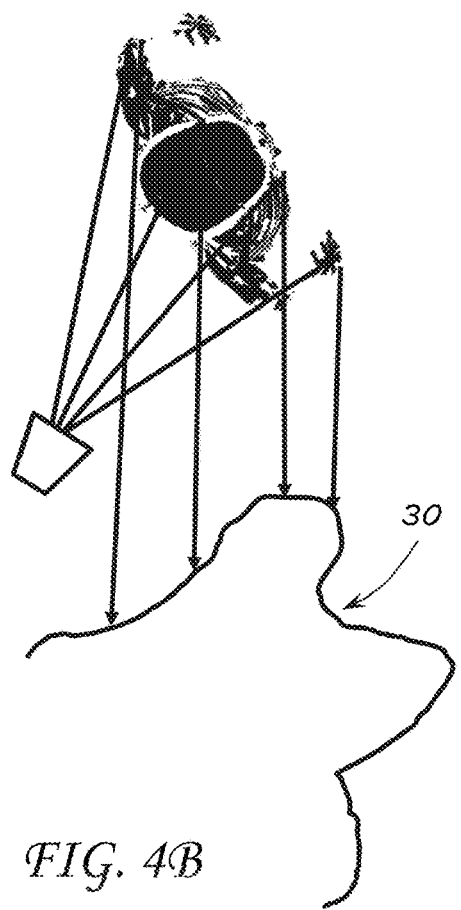
Figure 4D:
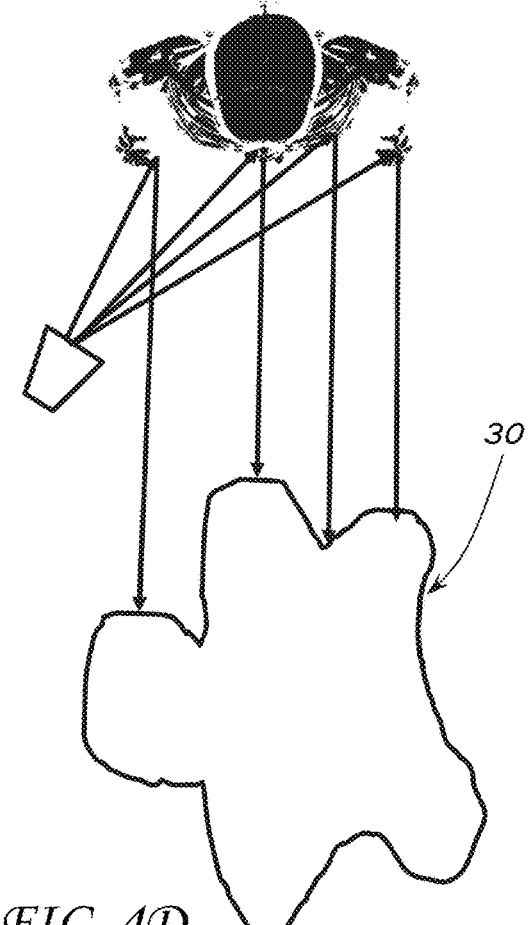
Figure 4C:
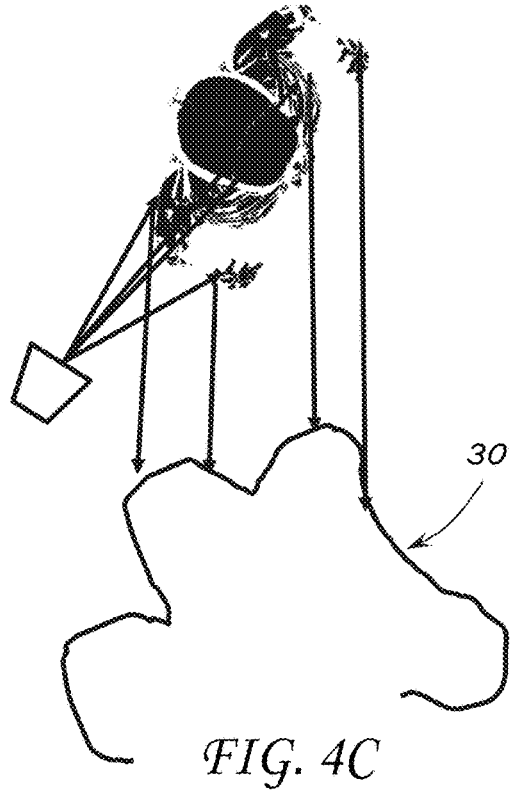

RADAR technology was originally developed to range and detect perfectly conductive objects such as metals and other man made materials. RADAR technology uses electromagnetic energy in the radio or microwave frequencies of the electromagnetic (EM) spectrum 10 as illustrated in FIG. 1. The EM spectrum 10 is illustrated as a number of bands: Radio 12 ($\lambda \sim 10^2$-$10^4$ cm), Microwave 14 ($\lambda \sim 1$ cm), Infrared 16 ($\lambda \sim 10^{-2}$ cm), Visible 18 ($\lambda \sim 10^{-5}$ cm), Ultraviolet 20 ($\lambda \sim 10^{-6}$ cm), X-Ray 22 ($\lambda \sim 10^{-8}$ cm), and Gamma Ray 24 ($\lambda \sim 10^{-10}$-$10^{-12}$ cm). This energy may be measured in terms of power spectral density (PSD). The Federal Communications Commission (FCC) is the United States' governing body for the electromagnetic spectrum. The FCC determines the PSD limits that may be used in a controlled or uncontrolled environment. The table in FIG. 2A illustrates limits for Occupational/Controlled Exposure and the table in FIG. 2B illustrates limits for General Population/Uncontrolled Exposure. ""f"" in both tables is frequency in MHz and the items indicated with * indicate plane-wave equivalent power density.

Occupational/controlled limits apply in situations in which persons are exposed because of their employment provided those persons are fully aware of the potential for exposure and can exercise control over their exposure. Limits for occupational/controlled exposure also apply in situations when an individual is transient through a location where occupational/controlled limits apply provided he or she is made aware of the potential for exposure. Conversely, general population/uncontrolled exposures apply in situations in which the public may be exposed, or in which persons that are exposed because of their employment may not be fully aware of the potential for exposure or cannot exercise control over their exposure. Many contemporary technologies, such as cell phones, GPS, computers, Wi-Fi, and Bluetooth, utilize the same operating EM spectrum as RADAR.

RADAR can be an optimal technology for detecting and ranging highly conductive materials such as metal. But, RADAR may be suboptimal technology for detecting and ranging dielectrics. Dielectric materials are electrical insulators and poor conductors. Dielectrics absorb electromagnetic energy. Any scattering of the energy is not from the surface, but rather somewhere internal to the dielectric, if there is any scattering at all.

RADAR works by sending out EM energy into the environment. As the RADAR wave propagates through space, the PSD decreases with distance from the source by a known quantity. When the RADAR wave encounters a highly conductive object, the RADAR wave scatters according to the objects size, orientation, shape, and material composition. This scattering may then be received by a RADAR receiver. When the RADAR wave encounters a dielectric, part of the RADAR wave is absorbed and any scattering occurs from somewhere inside the dielectric. Or, for some dielectric materials, all of the RADAR wave is absorbed and no scattering occurs.

Thus, it is very challenging to detect, range, and uniquely identify humans using low power RADAR operating from large distances to the human, especially since the energy is more likely to be absorbed than scattered from a human because human tissue is generally composed of dielectric materials. Thus, the absorption of scattering energy would not only be a detriment to an identification system but also to the human, especially at high PSDs. The effect of high PSD RADAR operating in the presence of a human is internal heating like that of a sunburn on exposed skin.

However, since human tissue is composed of known and well-documented frequency-dependent dielectric materials, embodiment of the invention take advantage of a way to safely collect radar scattering from a human that minimizes the heating effect while scattering the information needed for biometric identification. First, appropriate conditions were determined over which a RADAR waveform scatters maximally for a human while minimizing the internal heating. Human dielectric information was used to help find the appropriate conditions and those were tested on a phantom 24 illustrated in FIG. 3 representing the front 26 and top 28 of a human body. Using a specific RADAR waveform over a wide band of frequencies, an algorithm was developed to be used in embodiments of the invention that may assist in uniquely identifying a human from time-invariant human RADAR scattering features.

The human body is a complex biological system that contains tissue, bone, and organs with known permeability, conductivity, and permittivity. The human skeleton also has certain geometric structures that are quasi-symmetric along the azimuth direction. These known characteristics and biological features of human beings are leveraged in the embodiments of the invention.

It is well known that human skeletal features are unique biometric indices. X-ray technologies accurately measure and image the human skeleton, bone, and teeth. The problem with using X-ray as a biometric scanner is the human risk due to ionizing radiation. The World Health Organization has determined that long-term, even low dose, use of X-ray technology may lead to cancer. This is an unacceptable risk for a biometric technology. To develop a safe biometric radar system, embodiments of the invention use biological facts in combination with known electromagnetic theory.

In 1908, Mie wrote his seminal paper that solved for the scattering of a sphere analytically. From this solution, it was determined that RADAR scattering from certain azimuth-symmetric geometric shapes could not only be solved for analytically but its shape and size can be inferred from scattering measurements.

The human body has certain bones of known electromagnetic properties that will scatter as a Prolate-sphere or a cylinder at the UHF/VHF radar frequencies. In fact, because the symmetry of the human skeletal system is along the azimuth, orthogonal components of the skeleton will correlate and non-orthogonal components will have zero-correlation. As a result, the size of specific bones of the human body can be comparatively inferred from scattering information at a high resolution.

Human tissue dielectric properties have been determined by dosimetry testing. This information was used to determine the frequencies that would abide by our explicit constraints. See examples in Tables 1 and 2 below. Table 1 below illustrates penetration depth of RADAR waveforms for a number of human tissues at several frequencies.

TABLE 1

Tissue Dosimetry Table (Tissue, Frequency, and Penetration Depth)

|   | Tissue | Frequency | Penetration depth (m) |
|---|---|---|---|
| 1 | Cerebrospinal Fluid | 250 MHz | 0.02685 |
| 1 | Small Intestine | 250 MHz | 0.03093 |
| 2 | Gall Bladder Bile | 250 MHz | 0.033549 |
| 2 | Body Fluid | 250 MHz | 0.034897 |
| 2 | Eye (Vitreous Humor) | 250 MHz | 0.034897 |
| 2 | Blood | 250 MHz | 0.03895 |
| 2 | Cornea | 250 MHz | 0.042834 |
| 2 | Gall Bladder | 250 MHz | 0.04391 |
| 2 | Uterus | 250 MHz | 0.047653 |
| 2 | Eye (Sclera) | 250 MHz | 0.048063 |
| 2 | Retina | 250 MHz | 0.048063 |
| 2 | Prostate | 250 MHz | 0.048974 |
| 2 | Testes | 250 MHz | 0.048974 |
| 2 | Cerebellum | 250 MHz | 0.049689 |
| 2 | Kidney | 250 MHz | 0.050668 |
| 2 | Duodenum | 250 MHz | 0.050805 |
| 2 | Esophagus | 250 MHz | 0.050805 |
| 2 | Stomach | 250 MHz | 0.050805 |
| 2 | Spleen | 250 MHz | 0.051535 |
| 2 | Ovary | 250 MHz | 0.051544 |

TABLE 1-continued

Tissue Dosimetry Table (Tissue, Frequency, and Penetration Depth)

|   | Tissue | Frequency | Penetration depth (m) |
|---|---|---|---|
| 2 | Dura | 250 MHz | 0.052864 |
| 2 | Cervix | 250 MHz | 0.054571 |
| 2 | Gland | 250 MHz | 0.054912 |
| 2 | Lymph | 250 MHz | 0.054912 |
| 2 | Pancreas | 250 MHz | 0.054912 |
| 2 | Thymus | 250 MHz | 0.054912 |
| 2 | Thyroid | 250 MHz | 0.054912 |
| 2 | Heart | 250 MHz | 0.055718 |
| 2 | Muscle | 250 MHz | 0.058515 |
| 2 | Colon | 250 MHz | 0.059442 |
| 2 | Tongue | 250 MHz | 0.060728 |
| 3 | Lens | 250 MHz | 0.063719 |
| 3 | Trachea | 250 MHz | 0.065632 |
| 3 | Brain (Grey Matter) | 250 MHz | 0.066687 |
| 3 | Skin (Dry) | 250 MHz | 0.067124 |
| 3 | Lung (Deflated) | 250 MHz | 0.068034 |
| 3 | Mucous Membrane | 250 MHz | 0.068169 |
| 3 | Skin (Wet) | 250 MHz | 0.068169 |
| 3 | Liver | 250 MHz | 0.071588 |
| 3 | Cartilage | 250 MHz | 0.073234 |
| 3 | Tendon | 250 MHz | 0.074823 |
| 3 | Aorta | 250 MHz | 0.075692 |
| 3 | Blood Vessel | 250 MHz | 0.075692 |
| 3 | Lung (Inflated) | 250 MHz | 0.084744 |
| 3 | Bladder | 250 MHz | 0.08569 |
| 3 | Nerve | 250 MHz | 0.086399 |
| 3 | Spinal Cord | 250 MHz | 0.086399 |
| 3 | Brain (White Matter) | 250 MHz | 0.094028 |
| 4 | Bone (Cancellous) | 250 MHz | 0.13097 |
| 5 | Bone (Cortical) | 250 MHz | 0.25525 |
| 5 | Nail | 250 MHz | 0.25525 |
| 5 | Tooth | 250 MHz | 0.25525 |
| 6 | Fat | 250 MHz | 0.33498 |
| 7 | Breast Fat | 250 MHz | 0.4001 |
| 8 | Bone Marrow | 250 MHz | 0.4916 |
| † | Air | 250 MHz | 1.2 |
| † | Vacuum | 250 MHz | 1.2 |
| 1 | Cerebrospinal Fluid | 275 MHz | 0.026004 |
| 1 | Small Intestine | 275 MHz | 0.029819 |
| 2 | Gall Bladder Bile | 275 MHz | 0.032588 |
| 2 | Body fluid | 275 MHz | 0.034124 |
| 2 | Eye (Vitreous Humor) | 275 MHz | 0.034124 |
| 2 | Blood | 275 MHz | 0.037898 |
| 2 | Eye (Cornea) | 275 MHz | 0.041548 |
| 2 | Gall Bladder | 275 MHz | 0.042764 |
| 2 | Uterus | 275 MHz | 0.046395 |
| 2 | Eye (Sclera) | 275 MHz | 0.046868 |
| 2 | Eye (Retina) | 275 MHz | 0.046868 |
| 2 | Prostate | 275 MHz | 0.047756 |
| 2 | Testes | 275 MHz | 0.047756 |
| 2 | Cerebellum | 275 MHz | 0.04779 |
| 2 | Kidney | 275 MHz | 0.048704 |
| 2 | Ovary | 275 MHz | 0.049509 |
| 2 | Duodenum | 275 MHz | 0.049657 |
| 2 | Esophagus | 275 MHz | 0.049657 |
| 2 | Stomach | 275 MHz | 0.049657 |
| 2 | Spleen | 275 MHz | 0.049743 |
| 2 | Dura | 275 MHz | 0.051479 |
| 2 | Cervix | 275 MHz | 0.053314 |
| 2 | Gland | 275 MHz | 0.053754 |
| 2 | Lymph | 275 MHz | 0.053754 |
| 2 | Pancreas | 275 MHz | 0.053754 |
| 2 | Thymus | 275 MHz | 0.053754 |
| 2 | Thyroid | 275 MHz | 0.053754 |
| 2 | Heart | 275 MHz | 0.053767 |
| 2 | Muscle | 275 MHz | 0.05721 |
| 2 | Colon | 275 MHz | 0.057602 |
| 2 | Tongue | 275 MHz | 0.059311 |
| 2 | Eye (Lens) | 275 MHz | 0.062352 |
| 9 | Trachea | 275 MHz | 0.063973 |
| 9 | Skin (Dry) | 275 MHz | 0.064447 |
| 9 | Brain (Grey Matter) | 275 MHz | 0.064459 |
| 9 | Mucous Membrane | 275 MHz | 0.066012 |
| 9 | Skin (Wet) | 275 MHz | 0.066012 |
| 9 | Lung (Deflated) | 275 MHz | 0.06618 |
| 9 | Liver | 275 MHz | 0.069116 |
| 9 | Cartilage | 275 MHz | 0.071159 |
| 9 | Tendon | 275 MHz | 0.073267 |
| 9 | Aorta | 275 MHz | 0.073764 |
| 9 | Blood Vessel | 275 MHz | 0.073764 |
| 9 | Lung (Inflated) | 275 MHz | 0.08213 |
| 9 | Nerve | 275 MHz | 0.083527 |
| 9 | Spinal Cord | 275 MHz | 0.083527 |
| 9 | Bladder | 275 MHz | 0.083634 |
| 9 | Brain (White Matter) | 275 MHz | 0.090859 |
| 10 | Bone (Cancellous) | 275 MHz | 0.12665 |
| 11 | Bone (Cortical) | 275 MHz | 0.24692 |
| 11 | Nail | 275 MHz | 0.24692 |
| 11 | Tooth | 275 MHz | 0.24692 |
| 6 | Fat | 275 MHz | 0.32983 |
| 7 | Breast Fat | 275 MHz | 0.39385 |
| 8 | Bone Marrow | 275 MHz | 0.48035 |
| † | Air | 275 MHz | 1.09 |
| † | Vacuum | 275 MHz | 1.09 |
| 1 | Cerebrospinal Fluid | 800 MHz | 0.019752 |
| 1 | Small Intestine | 800 MHz | 0.020784 |
| 1 | Gall Bladder Bile | 800 MHz | 0.025625 |
| 1 | Body fluids | 800 MHz | 0.028275 |
| 1 | Eye (Vitreous Humor) | 800 MHz | 0.028275 |
| 1 | Blood | 800 MHz | 0.028832 |
| 1 | Eye (Cornea) | 800 MHz | 0.030305 |
| 2 | Kidney | 800 MHz | 0.031594 |
| 2 | Ovary | 800 MHz | 0.031786 |
| 2 | Cerebellum | 800 MHz | 0.031922 |
| 2 | Spleen | 800 MHz | 0.033874 |
| 2 | Gall Bladder | 800 MHz | 0.034133 |
| 2 | Uterus | 800 MHz | 0.034727 |
| 2 | Eye (Sclera) | 800 MHz | 0.035867 |
| 2 | Eye (Retina) | 800 MHz | 0.035867 |
| 2 | Heart | 800 MHz | 0.035901 |
| 2 | Prostate | 800 MHz | 0.036221 |
| 2 | Testes | 800 MHz | 0.036221 |
| 2 | Duodenum | 800 MHz | 0.038188 |
| 2 | Esophagus | 800 MHz | 0.038188 |
| 2 | Stomach | 800 MHz | 0.038188 |
| 2 | Dura | 800 MHz | 0.039101 |
| 2 | Colon | 800 MHz | 0.039999 |
| 2 | Cervix | 800 MHz | 0.041299 |
| 2 | Gland | 800 MHz | 0.041745 |
| 2 | Lymph | 800 MHz | 0.041745 |
| 2 | Pancreas | 800 MHz | 0.041745 |
| 2 | Thymus | 800 MHz | 0.041745 |
| 2 | Thyroid | 800 MHz | 0.041745 |
| 2 | Skin Dry | 800 MHz | 0.04223 |
| 2 | Brain (Grey Matter) | 800 MHz | 0.043767 |
| 2 | Muscle | 800 MHz | 0.044095 |
| 2 | Tongue | 800 MHz | 0.044675 |
| 2 | Mucous Membrane | 800 MHz | 0.045592 |
| 2 | Skin Wet | 800 MHz | 0.045592 |
| 2 | Liver | 800 MHz | 0.045674 |
| 2 | Lung (Deflated) | 800 MHz | 0.047268 |
| 2 | Trachea | 800 MHz | 0.047409 |
| 2 | Cartilage | 800 MHz | 0.047994 |
| 2 | Eye (Lens) | 800 MHz | 0.048254 |
| 2 | Tendon | 800 MHz | 0.053661 |
| 2 | Aorta | 800 MHz | 0.054226 |
| 2 | Blood Vessel | 800 MHz | 0.054226 |
| 2 | Nerve | 800 MHz | 0.05646 |
| 2 | Spinal | 800 MHz | 0.05646 |
| 2 | Lung (Inflated) | 800 MHz | 0.058206 |
| 2 | Brain (White Matter) | 800 MHz | 0.060062 |
| 9 | Bladder | 800 MHz | 0.063953 |
| 9 | Bone (Cancellous) | 800 MHz | 0.077826 |
| 4 | Bone (Cortical) | 800 MHz | 0.14388 |
| 4 | Nail | 800 MHz | 0.14388 |
| 4 | Tooth | 800 MHz | 0.14388 |
| 5 | Fat | 800 MHz | 0.25619 |
| 5 | Breast Fat | 800 MHz | 0.27384 |

TABLE 1-continued

Tissue Dosimetry Table (Tissue, Frequency, and Penetration Depth)

| | Tissue | Frequency | Penetration depth (m) |
|---|---|---|---|
| 6 | Bone Marrow | 800 MHz | 0.3315 |
| † | Air | 800 MHz | 0.38 |
| † | Vacuum | 800 MHz | 0.38 |

A resolution cell, shown in Table 2, is what embodiments of the invention use to differentiate data (or image/plot/graph). There are multiple bits of information, (e.g., where the heart tissue is relative to eye), known dosimetry (permittivity, conductivity and permeability) results and the RADAR's range resolution at a specific frequency. Table 2 illustrates that at a specific frequency, tissues with similar penetration distances cannot be differentiated. Thus, these items fall into a specific resolution cell for a certain frequency. This resolution cell is important because when the results from multiple frequencies are combined, different azimuth angles and elevation angles, then a system of equations can be uniquely solved, which can assist in isolating a certain feature of a specific person. For example, two individuals have approximately the same height but one has a longer torso and that individual's legs are shorter than the other individual. So, the organs for these two individuals are going to show up in different locations, at different frequencies and at different azimuths (and elevations if available).

TABLE 2

Tissue Dosimetry Resolution Cell Legend

Resolution Cells

| | | |
|---|---|---|
| 0 | 0.0314 | 1 |
| 0.0314 | 0.0628 | 2 |
| 0.0628 | 0.0942 | 9 |
| 0.0942 | 0.1256 | 10 |
| 0.1256 | 0.157 | 4 |
| 0.157 | 0.1884 | 3 |
| 0.1884 | 0.2198 | — |
| 0.2198 | 0.2512 | 11 |
| 0.2512 | 0.2826 | 5 |
| 0.2826 | 0.314 | — |
| 0.314 | 0.3454 | 6 |
| 0.3454 | 0.3768 | — |
| 0.3768 | 0.4082 | — |
| 0.4082 | 0.4396 | 7 |
| 0.4396 | 0.471 | — |
| 0.471 | 0.5024 | 8 |
| 3.768 | 4.2704 | † |

Thus, a resolution cell is a unique identifier or RADAR-based signature. When the RADAR wave scatters from a cavity or rotational invariant object (such as the skull, limbs, ribcage and pelvis) of radius R, the resulting "peak" in the range-intensity plot will be associated with a specific frequency (f) and azimuthal angle (θ). Because a frequency (f) is related with a wavelength (λ) via f=c/λ (where c=3×10$^8$ m/s is the speed of light) and because resonant scattering occurs when R~λ. From this information, a biometric RADAR signature can be constructed. The resolution cell, which is associated with the "polar plot" that is a "template radar signature," is unique to an individual. The mathematical model set forth below may assist in finding an initial guess for a resolution cell via two parameters, (a), (b). These parameters represent a semi-major axis (a) and a semi-minor axis (b) of an ellipse. Depending on the azimuthal angle the radar is illuminating, the (a) and (b) will be different for each individual. They may also be mapped onto a polar plot via an "osculating process" where each angle of the turntable provides a part of the polar plot via scattering waves and intensity maps. See the representations of the polar plot 30 in FIGS. 4A-4D. The dosimetry information (permittivity, conductivity, penetration depth and loss tangent) helps determine what bone (location) the peak is from. The polar plot is thus the unique biometric RADAR footprint of a person.

Many human bones resemble cylinders and Prolate-spheres of varying sizes and orientations. Some bones resonate as dispersive cavities. Radar scattering features that resonate are most likely separable in the frequency domain because dispersive cavities scatter with large energies depending on the size of the cavity. To estimate size features from bone scattering and resonance, embodiments of the invention utilize adequate frequencies that would penetrate through fat and tissue deeply enough to scatter and resonate from bones. These embodiments also have a PSD that abides by the current FCC limits. These constraints required a RADAR system to be specifically designed for biometric scanning.

Thus, embodiments of the invention need to be wideband and frequency-agile, but also easily reconfigurable to work for any body type and weight. The low-frequency components have long wavelengths but poor resolution whereas the high frequency components have short wavelengths but high resolution. As a result, the wide bandwidth of the radar provides both depth and resolution without the need for a higher PSD.

It was not known if anthropometric ratios inferred from radar scattering of a human would be unique or time-invariant. A simple model was needed for the scattering of a human by a wide-band and low PSD RADAR system. The scattering for a human depends on certain anthropometric information as well an accurate estimate of the low-risk frequency-dependent PSD limits. The model developed for use in embodiments needs to be highly accurate in the frequency domain. This was addressed with the following nonstandard human scattering mathematical model:

$$E^s = \sum_{m=1}^{M} \pi \frac{E_0^2}{k_2^2} \sqrt{\frac{\epsilon_2}{\mu_2}} \sum_{n=1}^{\infty} (2n+1)(|a_n^m|^2 + |b_n^m|)^2 \quad (1)$$

where $$a_n^m = \frac{\frac{1}{\rho} jj_{ns2} - \frac{1}{N\rho} jj_{ns1}}{2inj y_{nn2} + \frac{1}{\rho} jj_{ns2} + \frac{i}{\rho} jy_{ns2} + \frac{1}{N\rho} jj_{ns1} - \frac{1}{N\rho} yy_{ns1}} \quad (2)$$

$$b_n^m = \frac{-\frac{1}{N\rho} jj_{ns1} + njj_{nn1} - \frac{N^2}{\rho} jj_{ns2} + nN^2 jj_{nn1}}{\frac{1}{N} jj_{ns1} - \frac{N^2}{\rho} jj_{ns2} - \frac{iN^2}{\rho} jy_{sn2} +} \quad (3)$$

$$\frac{1}{N\rho} jy_{ns2} + (N^2n - n)jj_{nn1} + i(N^2n - n)jy_{nn2}$$

and where $$jj_{nn1} = j_n(\rho)j_n(N\rho) \quad (4)$$

$$jj_{ns1} = j_n(\rho)j_{n-1}(N\rho) \quad (5)$$

$$jj_{nn2} = j_n(N\rho)j_{n-1}(\rho) \quad (6)$$

$$jy_{ns2} = j_n(N\rho)y_{n-1}(\rho) \quad (7)$$

-continued $$jy_{nn2} = j_n(N\rho)y_n(\rho) \quad (8)$$

$$jy_{sn2} = j_{n-1}(N\rho)y_n(\rho) \quad (9)$$

such that
1. The functions $j_n(\rho)$ and $y_n(\rho)$ are spherical Bessel functions of the first and second kind, respectively.
2. The spherical Bessel functions generalize to Sinc functions of $\rho$.
3. As s and n increase, the modes become more oscillatory and induce an extinction, in this case, of $\rho$.

Those extinctions represent the boundaries between layered permittivity materials, or in the case of the bone location and size biometric authentication, can be measured as physical features of the resonating objects and their associated cavities.

Thus, by setting the human tissue boundaries to zero, the resonant scattering frequencies may be determined for a human in a radar test-range environment. Then, approximations can be made to determine the features and data components that would-be time-invariant and useful for biometric authentication. These approximations are equivalent to a Gabor filter.

Conceptually the electromagnetic (EM) wave propagates through the air until it reaches the boundary of the first dispersive tissue, which is skin. Since the maximum skin depth for wet or dry skin is between 0.02-0.06 m, and the energy decays and gets perturbed as the wave propagates through the medium, the first reflection from the air to skin boundary will be primary in the time domain and will correspond to frequencies associated to small wavelengths.

As the wave penetrates further into the tissue, its energy decreases exponentially depending on specific human parameters (e.g., size of fat layer and thickness of skin). It is interesting to note that bones cover most major organs. Thus, the tissues that generally need to be penetrated with radar are fat, muscle, and some of the circulatory system.

Another interesting fact is that wave propagation in fat decays slower than wave propagation in muscle. In fact, the ratio of loss is 3-to-1 for muscle-to-fat. This means that a mathematical relationship may be constructed between size, material, and resolution for the human body. See Tables 1 and 2 above. The muscles also have a property that they are shaped like cylinders that lie in orthogonal orientations, such as horizontal or vertical, for different elevations in the human body. This means that height is an estimate that may be inferred without the need for many elevation measurements.

Another advantage of the human body as a RADAR scattering object is that it stores and interacts with RADAR energy in such a way that the active RADAR's incoming power will interact with the human body's stored radiative energy, particularly from the adenosine triphosphate (ATP) produced by mitochondria, which are stored in fat (adipose) and other nucleus containing cells and tissue. Accordingly, the frequencies chosen to be used with embodiments of the invention have wavelengths that are approximately the size of the human body features of interest. This assists in ensuring that the scattering from bones will be the largest due to the body's own stored energy (which can easily be collected by a passive receiving antenna) and the resonance-based features that results from the active RADAR's PSD. Thus, the scattering measurements should be unique to an individual. However, the RADAR energy still needs to be constrained to ensure safety and not overheat human tissue.

The time-invariant human scattering needs to be determined next. Thus, the material properties need to be linear. As can be seen from the coefficients, $a_n^m$ and $b_n^m$, although Maxwell's equations are linear, the scattering function may not be globally linear. However, there is local linearity at the resonance regions. The resonance regions are determined by optimizing (max) both coefficients of the stable skeletal features.

The model was compared to commercial off-the-shelf, phantom, and human radar scattering data, which validated that the model accurately represents the scattering from the important features that are needed for building the RADAR and developing a classification method.

Once the model was verified, the model was used to determine the specific parameters needed to design a RADAR system that was optimized for biometric identification. The RADAR system has also been designed to optimize the quality of the data collection. An anechoic chamber used for testing minimizes any multiple scattering during the data collection. The RADAR system is composed of two impulse antennas that operate between approximately 250 MHz to 20 GHz. The operational frequencies of the radar are 250 MHz-20 GHz but may be changed to accommodate FCC compliance.

Figure 5:
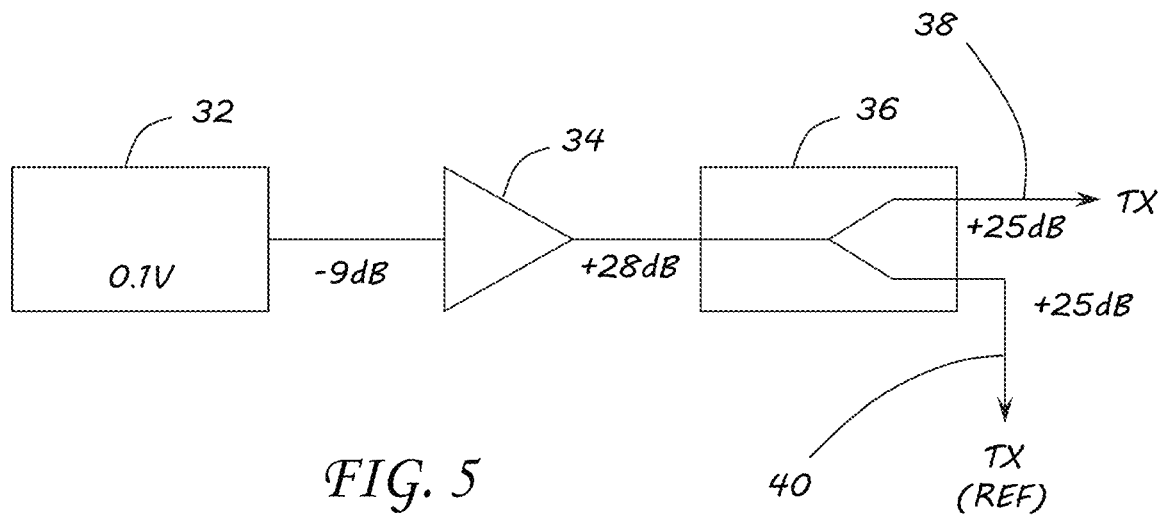
FIG. 5 is a schematic block diagram of a transmitter setup with calculated powers illustrated.

In an exemplary embodiment, RADAR antennas may be mounted inside the anechoic chamber. The anechoic chamber contains RADAR-absorbing material. The antennas in the exemplary embodiment are mounted on a rotational track along the wall of the chamber to scan the subject, enabling a faster data collection. The antennas are connected to a control system and the RADAR 32 externally through an amplifier 34 and splitter 36 via low-loss cables to produce transmit (TX) 38 and reference TX 40 signals as illustrated in FIG. 5.

Figure 6:
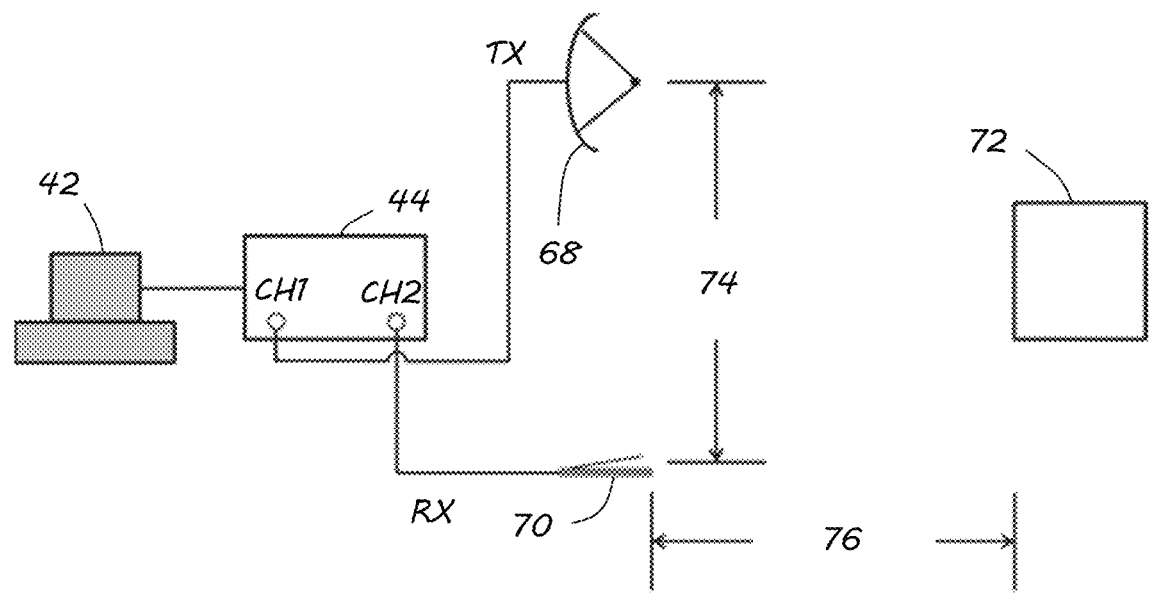
FIG. 6 is a schematic block diagram of a system used for obtaining and processing the radar data.
Figure 7:
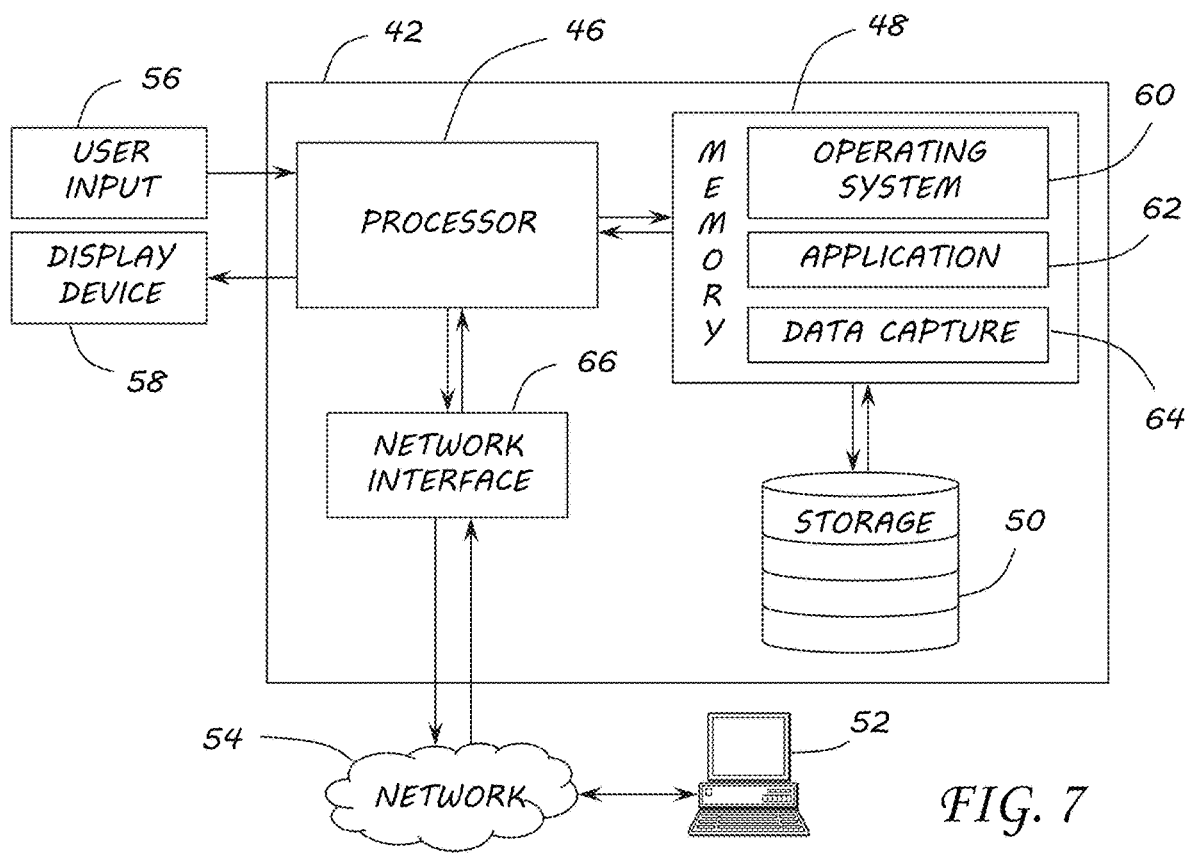
FIG. 7 is an exemplary hardware and software environment for determining and detecting scattering characteristics consistent with embodiments of the invention.

A block diagram of an exemplary embodiment of the invention is shown in FIG. 6. A controller 42 or other type specialized analysis device may be connected to and receive data from a vector network analyzer 44. FIG. 7 illustrates an exemplary hardware and software environment for a computing device 42 suitable for performing analysis in a manner consistent with the invention. For the purposes of the invention, computing device 42 may represent practically any computer, computer system, or programmable device, e.g., multi-user or single-user computers, desktop computers, portable computers and devices, handheld devices, network devices, mobile phones, etc. Computing device 42 will hereinafter be referred to simply as a "computer" although it should be appreciated that the term "controller" may also include any other suitable programmable electronic devices.

Controller 42 typically includes at least one processor 46 coupled to a memory 48. Processor 46 may represent one or more processors (e.g. microprocessors), and memory 48 may represent the random access memory (RAM) devices comprising the main storage of controller 42, as well as any supplemental levels of memory, e.g., cache memories, non-volatile or backup memories (e.g. programmable or flash memories), read-only memories, etc. In addition, memory 48 may be considered to include memory storage physically located elsewhere in controller 42, e.g., any cache memory in a processor 46, as well as any storage capacity used as a virtual memory, e.g., as stored on a mass storage device 50 or another computer 52 coupled to controller 42 via a network 54 or other means. The mass storage device 50 may contain a cache or other dataspace, which may be used to store and manipulate data received from network analyzer 44 (FIG. 6).

Controller 42 also typically receives a number of inputs and outputs for communicating information externally. For interface with a user or operator, controller 42 typically includes one or more user input devices 56 (e.g., a keyboard, a mouse, a trackball, a joystick, a touchpad, touch screen, a keypad, a stylus, and/or a microphone, among others). controller 42 may also include a display 58 (e.g., a CRT monitor, an LCD display panel, and/or a speaker, among others). The interface to controller 42 may also be through an external device connected directly or remotely to controller 42, or through another computer 52 communicating with controller 42 via a network 54 or other type of high speed communications device.

Controller 42 operates under the control of an operating system 60, and executes or otherwise relies upon various computer software applications, components, programs, objects, modules, data structures, etc. (e.g. Application 62 and Data Capture 64). The Application 62, for example, may analyze captured data to determine a scattering signature of an individual. Controller 42 communicates on the network 54 through a network interface 66.

In general, the routines executed to implement the embodiments of the invention, whether implemented as part of an operating system or a specific application, component, program, object, module or sequence of instructions will be referred to herein as "computer program code", or simply "program code". The computer program code typically comprises one or more instructions that are resident at various times in various memory and storage devices in a computer, and that, when read and executed by one or more processors in a computer, causes that computer to perform the steps necessary to execute steps or elements embodying the various aspects of the invention. Moreover, while the invention has and hereinafter will be described in the context of fully functioning computers and computer systems, those skilled in the art will appreciate that the various embodiments of the invention are capable of being distributed as a program product in a variety of forms, and that the invention applies equally regardless of the particular type of computer readable media used to actually carry out the distribution. Examples of computer readable media include but are not limited to non-transitory physical, recordable type media such as volatile and non-volatile memory devices, floppy and other removable disks, hard disk drives, optical disks (e.g., CD-ROM's, DVD's, etc.), among others; and transmission type media such as digital and analog communication links.

In addition, various program code described hereinafter may be identified based upon the application or software component within which it is implemented in specific embodiments of the invention. However, it should be appreciated that any particular program nomenclature that follows is merely for convenience, and thus the invention should not be limited to use solely in any specific application identified and/or implied by such nomenclature. Furthermore, given the typically endless number of manners in which computer programs may be organized into routines, procedures, methods, modules, objects, and the like, as well as the various manners in which program functionality may be allocated among various software layers that are resident within a typical computer (e.g., operating systems, libraries, APIs, applications, applets, etc.), it should be appreciated that the invention is not limited to the specific organization and allocation of program functionality described herein.

Those skilled in the art will recognize that the exemplary environment illustrated in FIG. 7 is not intended to limit the present invention. Indeed, those skilled in the art will recognize that other alternative hardware and/or software environments may be used without departing from the scope of the invention.

Returning now to FIG. 6, independent channels CH1 and CH2 of the network analyzer 44 receive both the transmitted 68 RADAR spectrum as well as the reflected RADAR spectrum at receiver 70 from an individual on a turntable 72. In the exemplary embodiment illustrated in FIG. 6, the turntable 70 may be used to receive a better scattering signature from an individual. Additionally, the distances 74, 76 between the transmitter 68 and receiver 70 as well as the distance to the individual may vary according to the type and power of the RADAR signals transmitted. In this illustrated embodiment, the distances between the transmitter 68 and receive 70 is about 306 cm and the distance from the transmitter 68 to the turntable 72 is about 1,089 cm.

Figure 8:
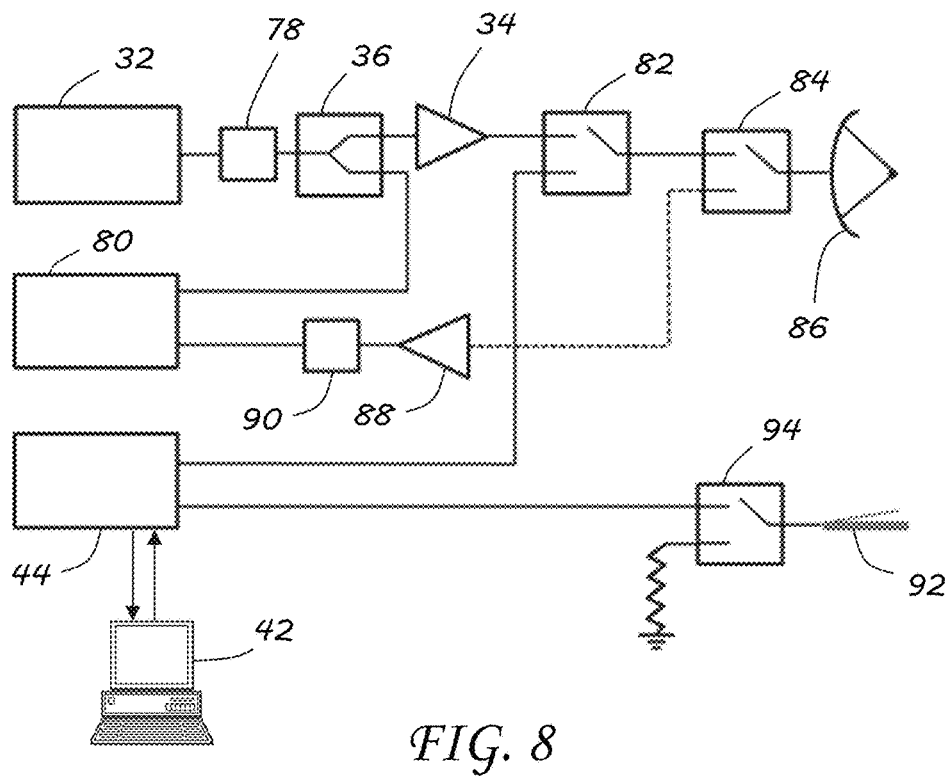
FIG. 8 is a schematic block diagram of an exemplary embodiments as illustrated in FIGS. 5 and 6.

FIG. 8 contains an additional schematic diagram of an exemplary embodiment of the invention, which essentially combines the schematics of FIGS. 5 and 6. In this exemplary embodiment, RADAR 32 sends an RF signal through low-pass filter 78 to the splitter 36. The signal is split into a transmit and reference signal (38, 40 in FIG. 5) with the reference being sent to one channel of a sampling oscilloscope 80. The transmit signal is then amplified by a power amplifier 34 prior to entering first system switch 82. The system switch is connected to a transmit/receive switch 84, which is connected to antenna 86, used to transmit and receive the signal the RF signal. Antenna 86 may be an IRA-3Q transmitting antenna with a 25 dB peak gain at 16 GHz and having a frequency range spanning 250 MHz to 18 GHz, though other embodiments may utilized other types of antennas. When switched to receive mode, the received RF signal is amplified by amplifier 88 and filtered by a band pass filter 90 before connecting to a second channel of the sampling oscilloscope 80. The signal is also fed to a first channel of network analyzer 44 and a signal received by a TEM receiver 92 is fed to a second channel of the network analyzer 44 through a second system switch 94.

Figure 9:
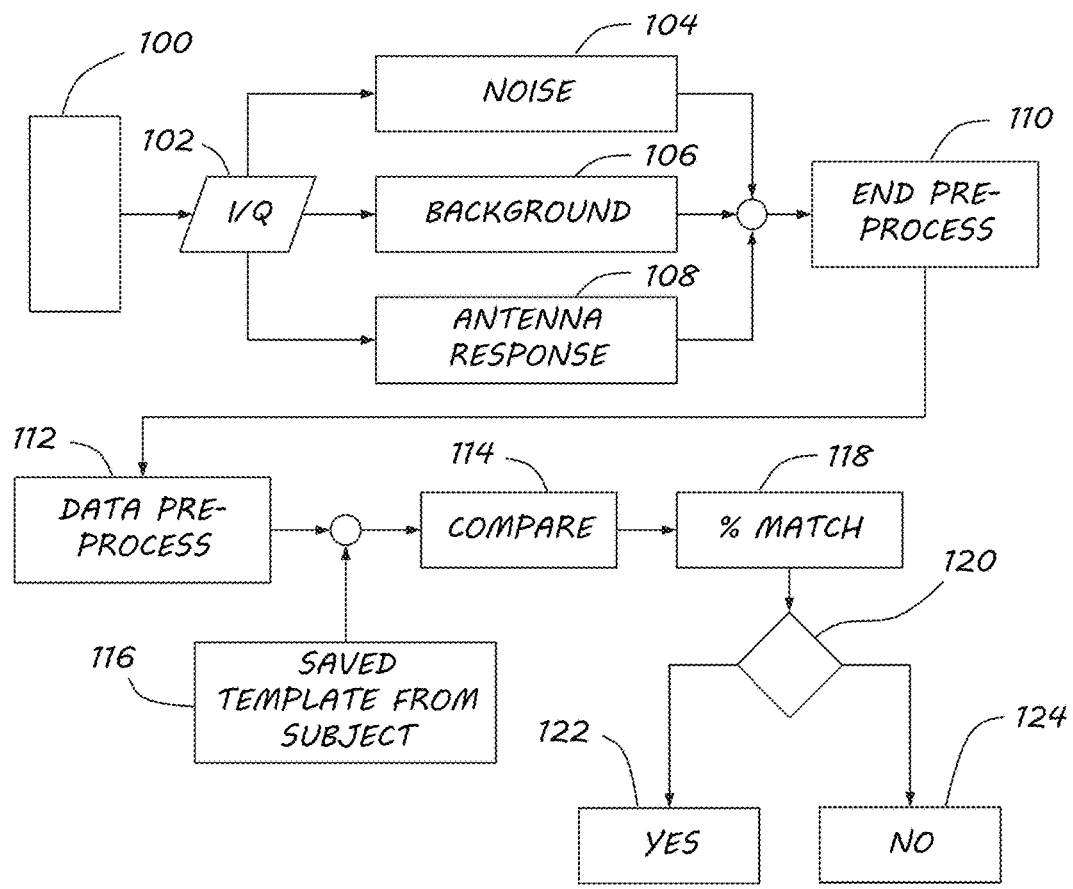
FIG. 9 is contains a data processing flow chart consistent with the operation of embodiments of the invention.

FIG. 9 illustrates the overall signal processing flow of an identification system, such as the system in the illustrated embodiment in FIG. 8. A processor 100, such as controller 42 in FIG. 8, collects and receives signal data 102, which is then pre-processed to "clean" the data. Noise may be removed in block 104. Background information may be removed in block 106. And, the antenna response may be removed in block 108. The pre-processing steps to "clean" the data is completed at block 110. The actual signal data of interest is then pre-processed in block 112 as discussed further below. This data is compared in block 114 against subject data that was saved in a template from block 116. The comparison results in a percent match in block 118. After passing or failing a threshold at decision block 120, the signal is identified as a match in block 122 or not a match in block 124.

Figure 10:
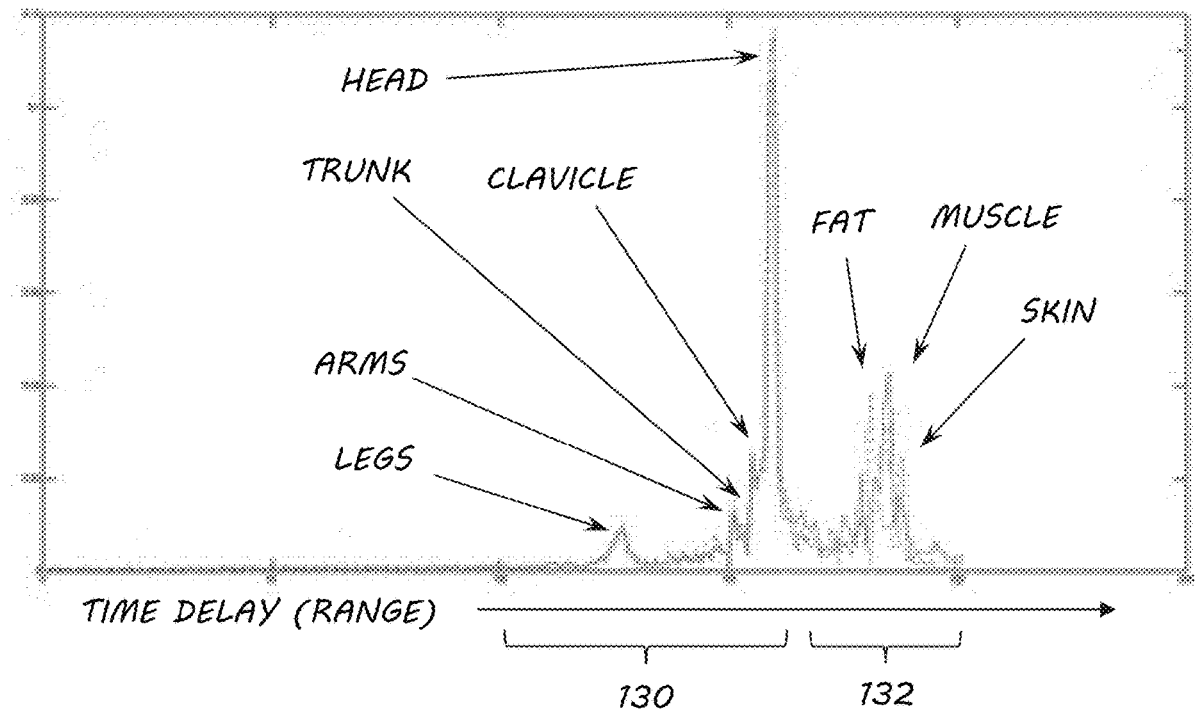
FIG. 10 is a representation of a data matrix utilized to organize data entries and avoid ambiguities.

The schematic in FIG. 10 graphically represents part of the process and further provides an exemplary representation of a data matrix and the principal steps in developing the data manipulation and extracting the unique feature data from the data set from the exemplary configuration in FIG. 9. The associated graph in FIG. 10 identifies some of the larger features in the frequency range indicated by 130 that are approximately time invariant. Changes to these bigger features are predicable over time. However, the features in the frequency range 132 are more time varying. Higher frequency/smaller time steps associated with these features means that these are smaller features that change more over time in angle, position, etc.

Any testing on human subjects requires that safety controls set by the FCC are abide by. The Maximum Permissible Exposure (MPE) limits are described in the FCC Rules and Regulations. For the frequency range of interest, the applicable limit for acceptable, continuous exposure of the general population and for "controlled" occupational exposure is outlined in FIGS. 2A and B. The tables in FIGS. 2A and 2B outline the FCC OET 65 guidance that states the maximum permissible exposure limits. FCC Bulletin OET 65 provides standardized formulas for calculating the power density that covers two areas of interest: (1) directly in front of the antenna; (2) at the face of the antenna; and (3) farther away from the antenna but still in the main beam. Each area of interest will be addressed below and the results of the calculation are given. Radiation limits on non-participants who are operating the static system are also addressed below.

In an alternate exemplary experimental setup, the transmitter of FIG. 6 is setup at a distance 76 of 730 cm from the turntable 72 and subject. During a pre-determined period, RF energy will be absorbed and may be accumulated by the subject. This is called Specific Absorption Rate (SAR). FCC limits the amount of exposure time to an average of 6 minutes for controlled exposure. The worst-case possible exposure occurs right at the surface of the antenna. The applicable formula for power density at the antenna surface is as follows.

$$S_{sa} = \frac{P}{A} \qquad (10)$$

where
$S_{sa}$=Power density at the Surface of the aperture
P=Power fed to the antenna
A=surface area of the antenna With 1000 mW of input power, an antenna area of approximately 117.5 cm², the power density at the antenna surface is approximately 8.51 mW/cm², which is above the MPE limit as stated in Table 3 below. Although the power density on the surface of the antenna is above the MPE limit, for safety purposes no person will be near the antenna aperture during the RADAR system's operation. The closest distance any person will be to the antenna during operation is approximately 80 cm. At 80 cm, at the highest transmit frequency, the power density is 0.043 mW/cm². This is far below the limit of 5.0 mW/cm². When technicians need to perform work in this area, standard RF safety procedures may be applied and power to the antenna will be removed during the period of the work.

Figure 11:
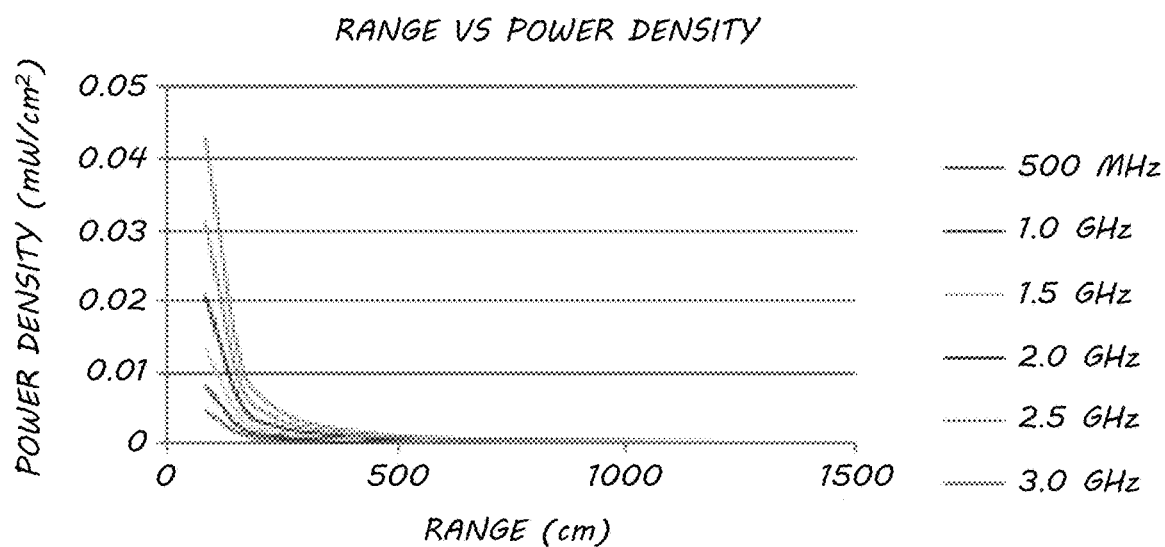
FIG. 11 contains a graph of range vs. power density plot for frequencies of interest consistent with embodiments of the invention.

In near-field region of the main beam, the power density can reach a maximum before it begins to decrease with distance. The range extent of the near-field could be described by the following equation:

$$R_{nf} = \frac{D^2}{4*\lambda} \qquad (11)$$

where
$R_{nf}$=Power density at the Surface of the aperture
D=Power fed to the antenna
λ=surface area of the antenna If D=0.47 m and λ=0.1 m the extent of the near-field is 4.23 m. Since the near-field range extent is frequency dependent this will be the maximum range of the near-field because the RADAR will operate from 250 MHz-3 GHz. In this region, the maximum near-field power density can be solved by using the following equation:

$$S_{nf} = \frac{16*\eta*P}{\pi*D^2} \qquad (12)$$

where
$S_{nf}$=maximum near-field power density
D=antenna diameter
P=power fed to antenna
η=aperture efficiency If an aperture efficiency of 85% is applied, the result of the calculation is approximately 1.96 mW/cm². This power is slightly above the MPE limit of 1.95 mW/cm², but as discussed above, no person will be within the near field of the antenna during its operation. Next are the calculations for power density in the far-field. The equation is as follows:

$$S(\theta) = \frac{PG(\theta)}{4\pi R^2} \qquad (13)$$

where
S(θ)=maximum near-field power density
P=antenna diameter
G(θ)=power fed to antenna
R=aperture efficiency FIG. 11 shows calculations of the power density at 730 cm for frequencies 250 MHz-3 GHz. The MPE limit is satisfied for each frequency.

Based on the result of the analysis and regarding the potential power density levels (1) at the aperture; (2) in the near-field region; (3) in the far-field region; and (4) for non-participants who operate the static VNA radar system, the static VNA radar system satisfies the MPE compliance requirements in the FCC regulations and standard safety procedures To improve the results of the test system in FIG. 6, measurements of the VNA 44 were made. Both VNA ports (CH1 and CH2) were terminated with a 50-Ω load and measurements were taken while varying the frequency from 250 MHz to 3 GHz. To estimate the Probability Density Function (PDF) of the VNA noise, some intermediate steps were taken. First, 10 sets of data were taken using the VNA. Each data set contained 1601 points. Next, the 10 data sets were combined to form a master dataset (16,010 points), which was used to calculate a data histogram. Then, the histogram was used as an estimate of the PDF of the VNA noise data. Lastly, MATLAB's® dfittool( ) function was used to fit the estimated PDF to a known distribution.

Figure 12A:
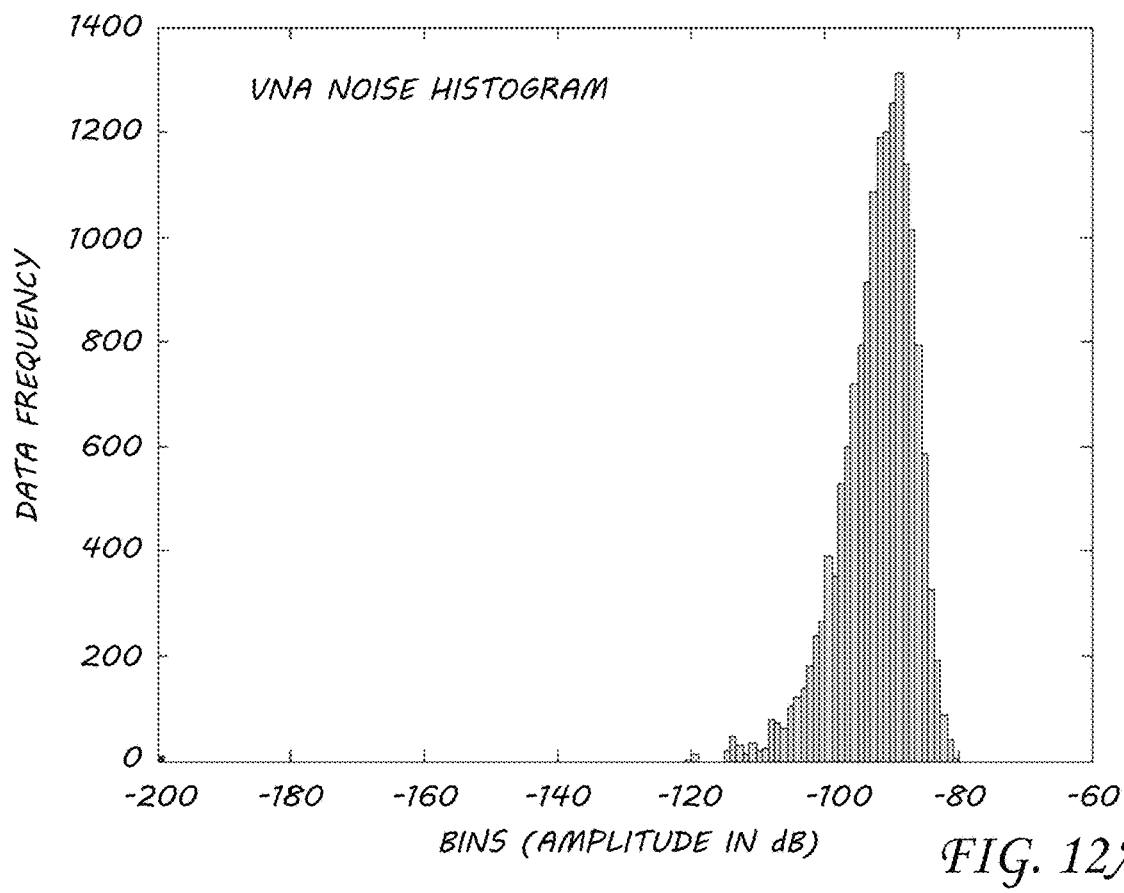
FIG. 12A is a histogram of VNA noise.

The plot shown in FIG. 12A shows a histogram of the VNA noise data. The noise data represents an important calibration step for the biometric test range. This step ensures that the biometric data collected for each authentication is not biased by system noise. The number of bins used in the original calibration function will be determined by using the following equation.

$$\# \text{Bins} = \sqrt{\# \text{of Datapoints}} \quad \# \text{Bins} = \sqrt{16,010} \approx 127 \text{ points} \qquad (4)$$

Figure 12B:
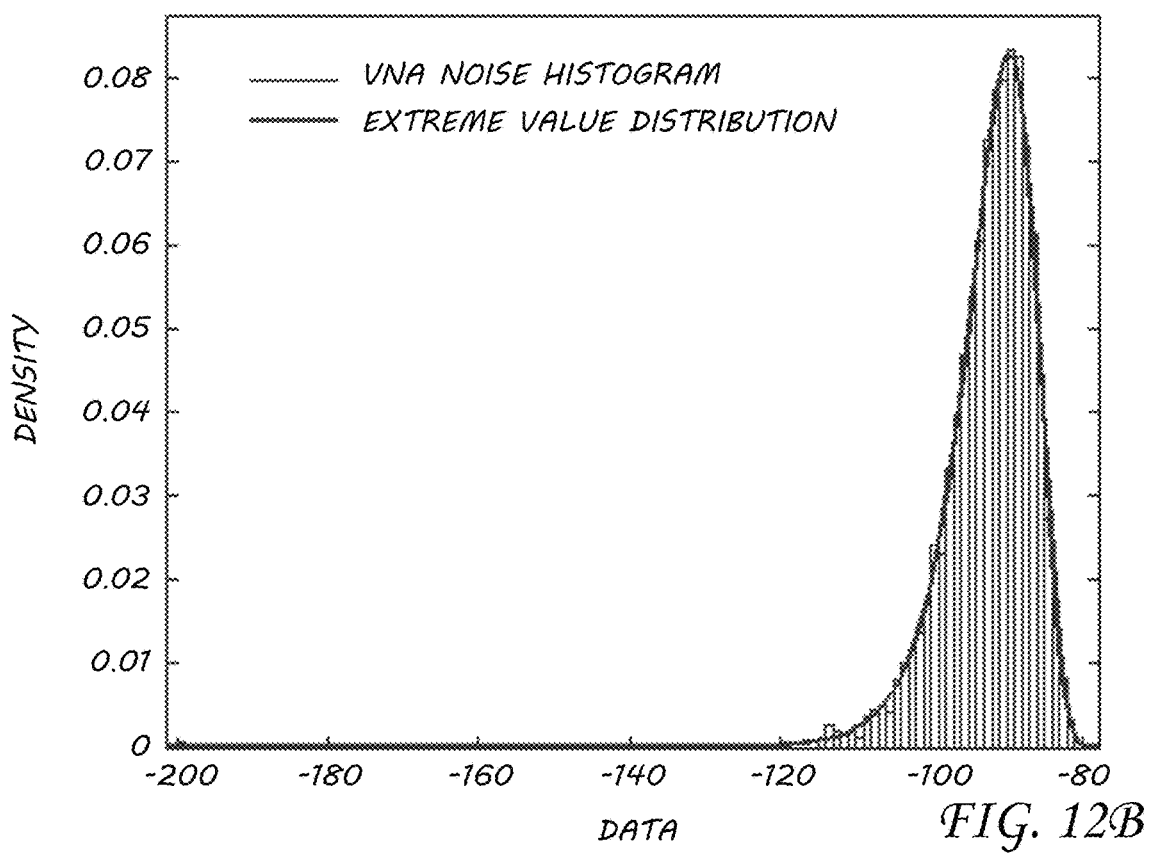
FIG. 12B is a graph of a curve fitted to the histogram of FIG. 12A.

Next, a known distribution is fit to the VNA noise histogram. FIG. 12B shows that the Extreme Value Distribution most closely approximates the distribution of the VNA noise histogram for a system used for biometric radar signatures. The equation below shows the equation for the Extreme Value Distribution.

$$y = f(x|\mu, \sigma) = \sigma^{-1} \exp\left(\frac{x-\mu}{\sigma}\right) \exp\left(-\exp\left(\frac{x-\mu}{\sigma}\right)\right) \quad (15)$$

The following measurements are made to examine experimental signal pulse widths, after system distortion due to cables and components. This is a calibration step for the peripheral system components to ensure biometric radar signature integrity. The experimental frequency-bandwidth is also measured in this step. According to Nyquist theorem, the theoretical bandwidth of a pulse is given by the following equation.

$$BW = \frac{1}{\text{pulse width}} \quad (16)$$

$$\text{Range Resolution} = \frac{c * \text{pulse width}}{2} \quad (17)$$

Note that c is the speed of light in m/s.

Table 3 below shows the calculated bandwidth and range resolution for the various pulse widths. FIGS. 14A-17B show the measured transmit pulses and the normalized spectrum magnitude as calculated using the spectral magnitude math display on the Tektronix DPO71254 using a flat plate test target.

TABLE 3

Transmit Pulse Theoretical Parameters

| Pulse Width (ps) | Theoretical Bandwidth (GHz) | Theoretical Range Resolution (mm) |
| --- | --- | --- |
| 83 ps | 12 | 12.45 |
| 100 ps | 10 | 15.00 |
| 200 ps | 5 | 30.00 |
| 250 ps | 4 | 37.50 |
| 333 ps | 3 | 49.95 |

Figure 13:
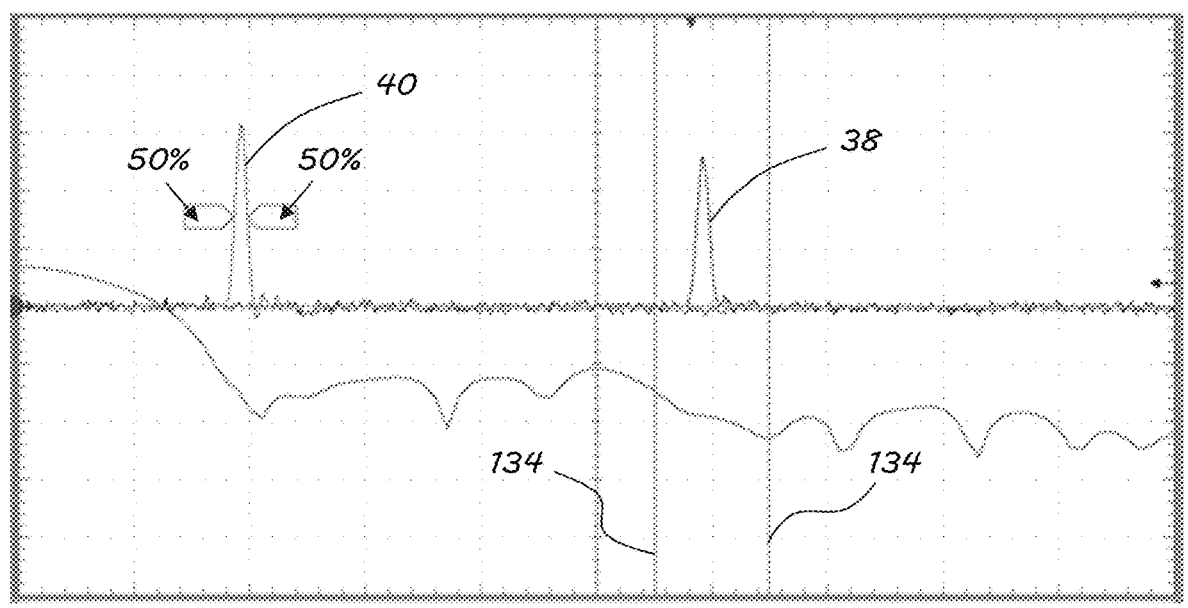
FIG. 13 is a reproduction of a measurement screen on an oscilloscope showing a transmit pulse spectrum.
Figure 14A:
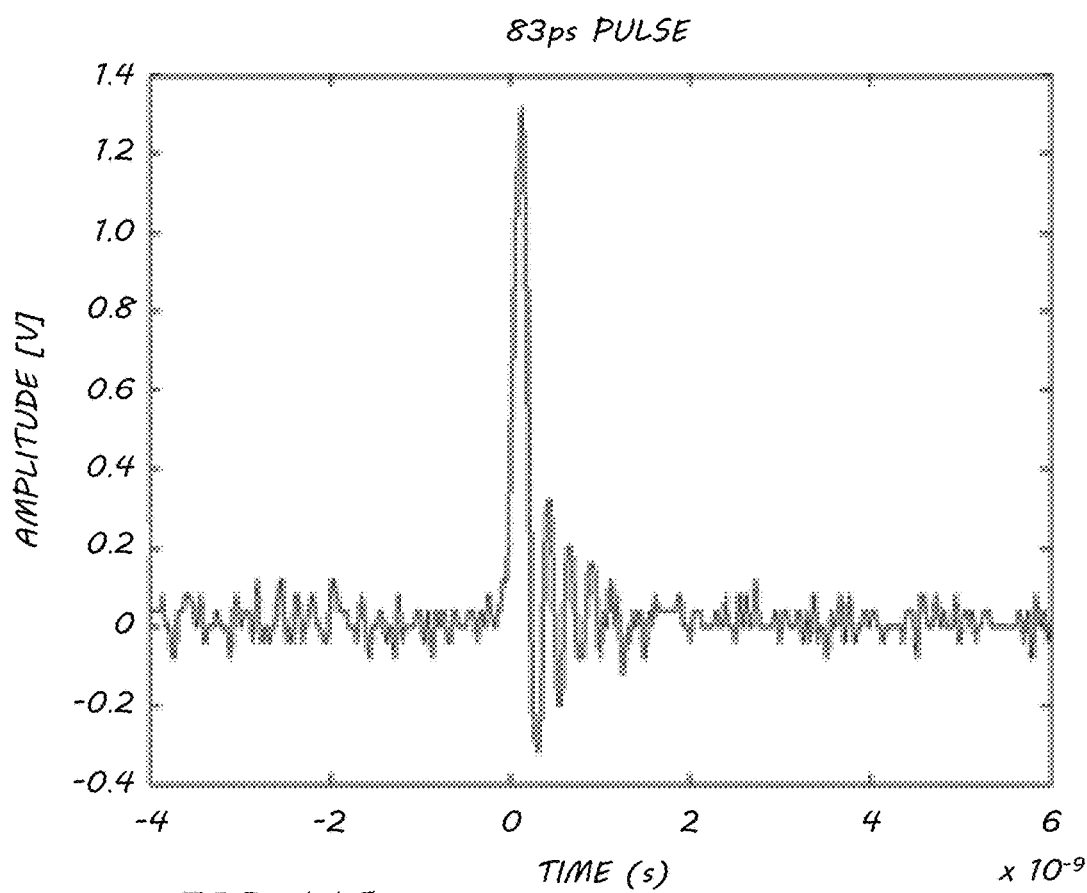
FIGS. 14A and 14B are graphs of an 83 ps pulse and corresponding magnitude spectrum respectively.
Figure 14B:
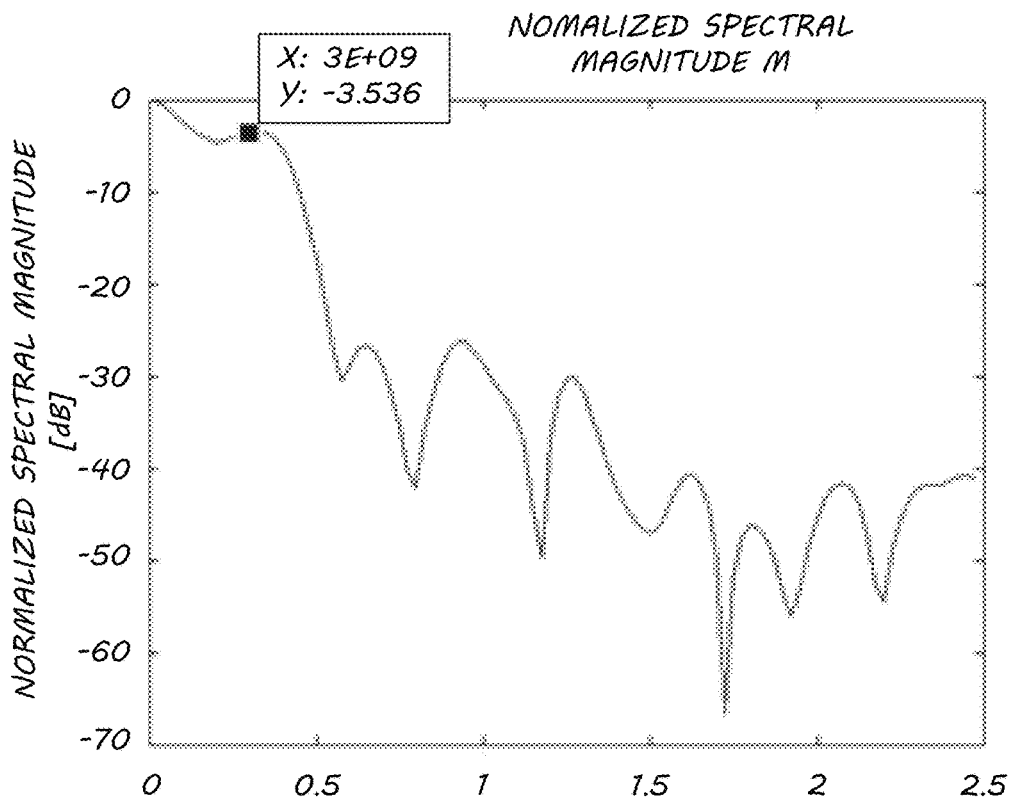
Figure 15A:
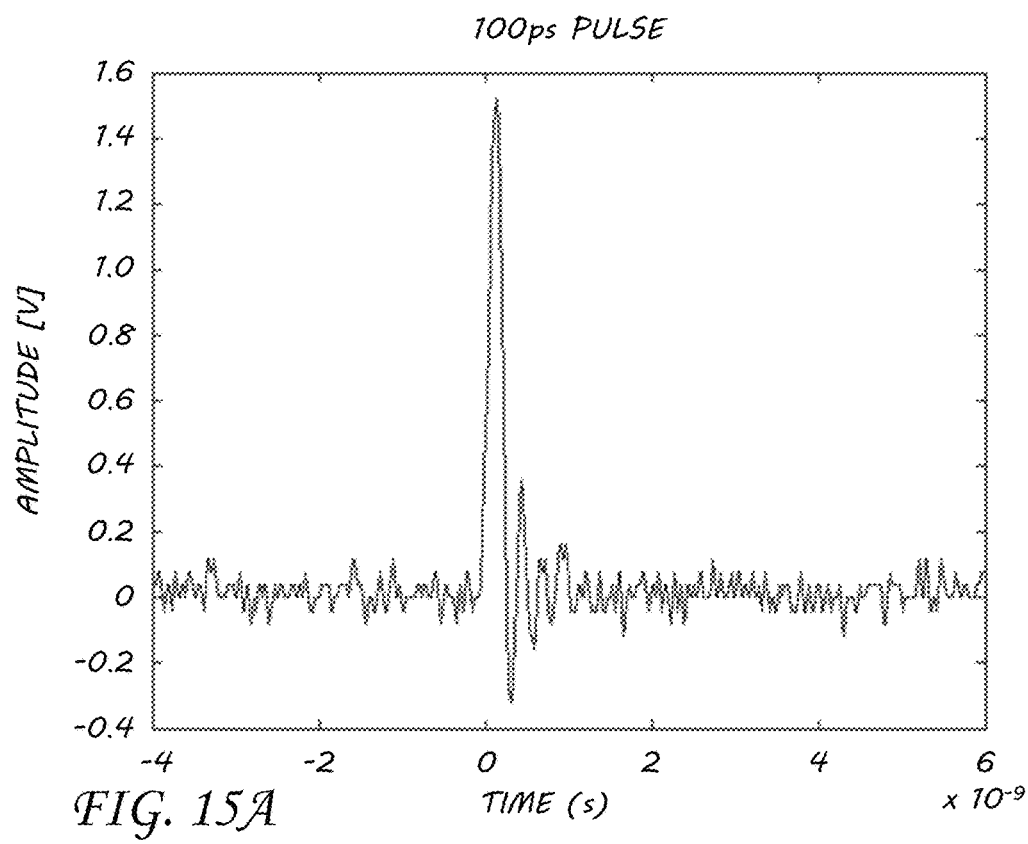
FIGS. 15A and 15B are graphs of an 100 ps pulse and corresponding magnitude spectrum respectively.
Figure 15B:
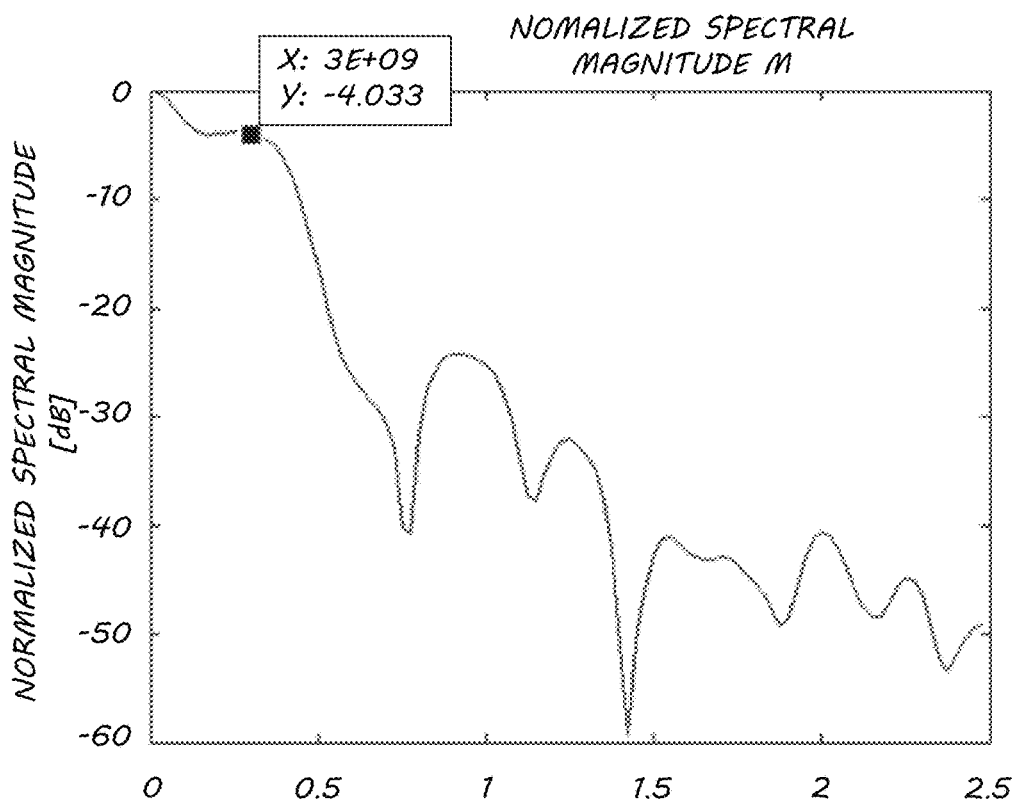
Figure 16A:
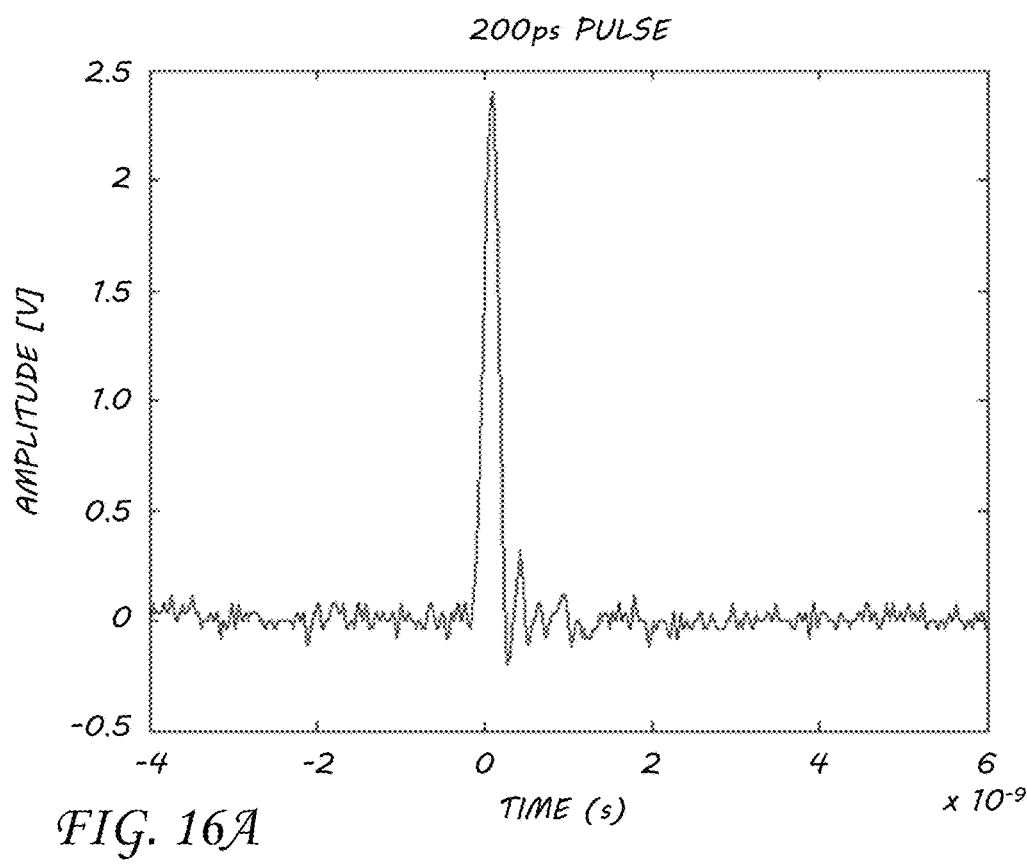
FIGS. 16A and 16B are graphs of an 200 ps pulse and corresponding magnitude spectrum respectively.
Figure 16B:
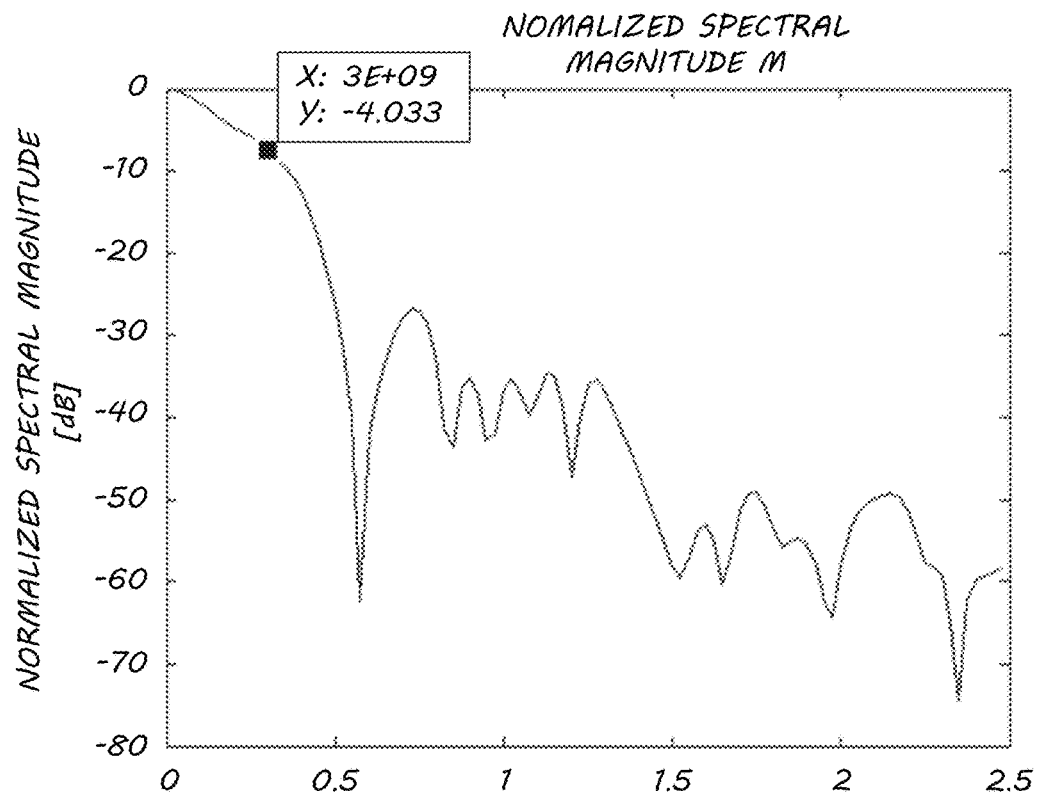
Figure 17A:
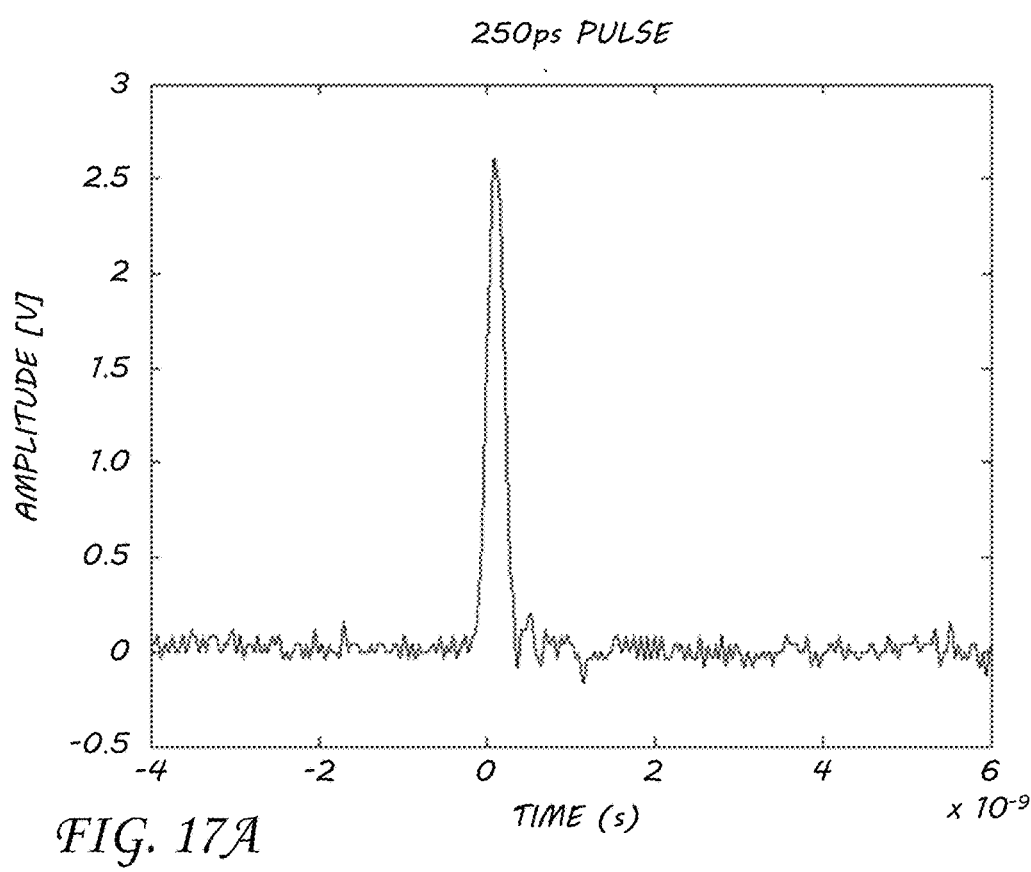
FIGS. 17A and 17B are graphs of an 250 ps pulse and corresponding magnitude spectrum respectively.
Figure 17B:
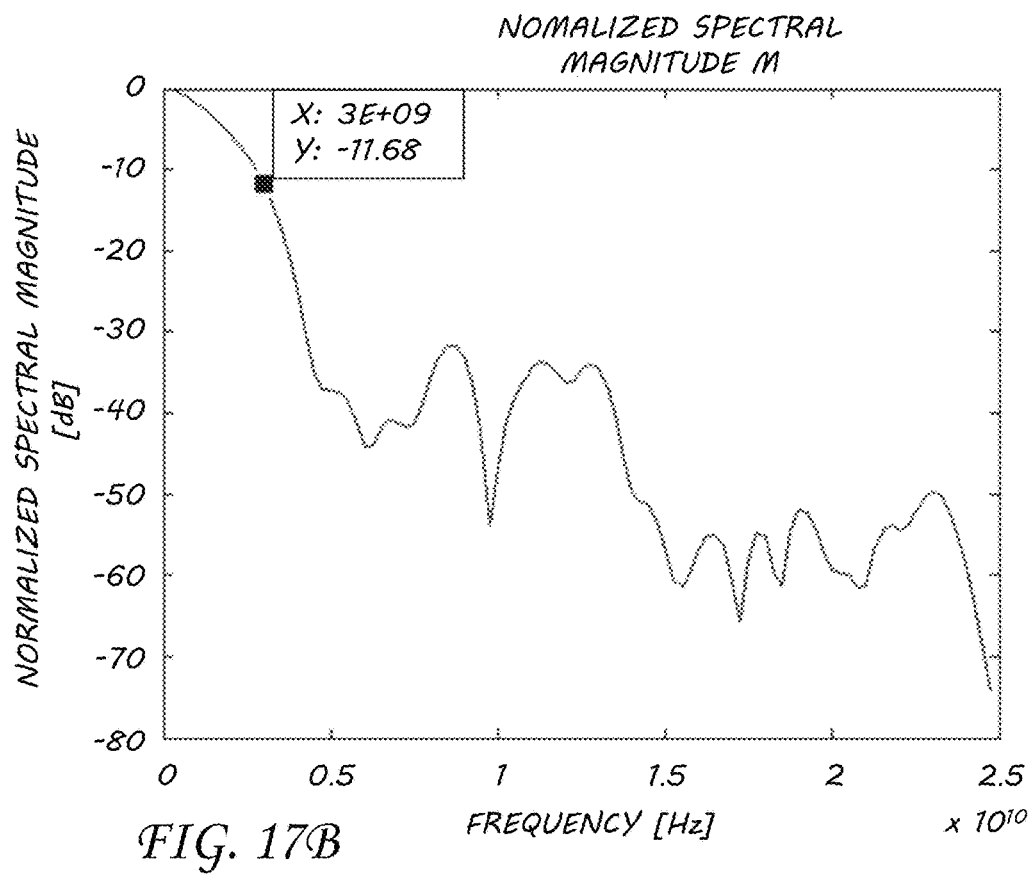

FIG. 13 shows a representation of the oscilloscope measurement screen. The transmit reference signal 40 and the transmit signal 38 are shown. The vertical bars 134 around the transmit signal 38 were used as a gate to calculate the signal spectrum.

Based on the results, the 200 ps or 250 ps transmit pulse will be used. The desired transmit signal bandwidth is approximately 250 MHz to 3 GHz, both the 200 ps and 250 ps transmit waveforms give acceptable bandwidths (approximately −10 dBm with a 3 dB bandwidth at 3 GHz).

The following measurements were made to examine the time delay between the transmit signal and transmit reference signal to assist in characterizing the system configuration. This step is required to ensure that the desired bandwidth is accurate for each subject template. Each subject will have his or her own bandwidth frequencies that will guarantee the most accurate data is collected for the subject. The following measurements represent a test subject with the equivalent radar cross-section of an average person of average height and weight. Measurements were taken with both 200 ps and 250 ps transmit pulses. There is approximately an 8 ns time delay between the 200 ps transmit and transmit reference signals. This time delay is approximately a 1.2 m (3.93 ft) path length difference. There is a 7.96 ns time delay between the 250 ps transmit and transmit reference signals. This time delay is approximately a 1.19 m (3.90 ft) path length difference.

Figure 18:
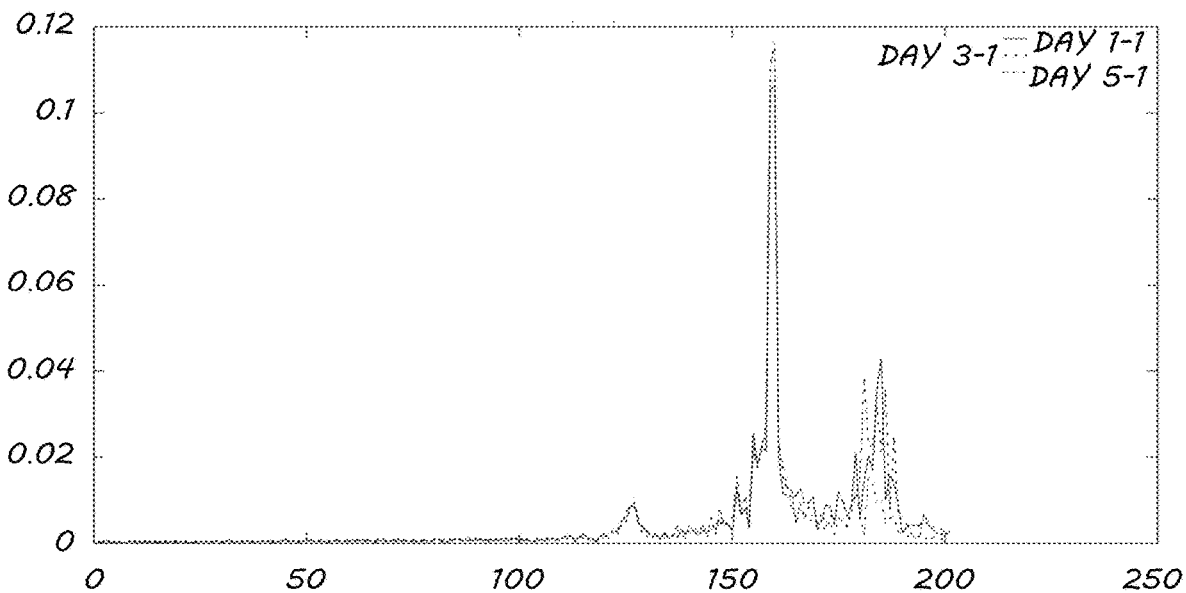
FIG. 18 is a graph of data from a test subject smoothed and centered to align with a peak.
Figure 19:
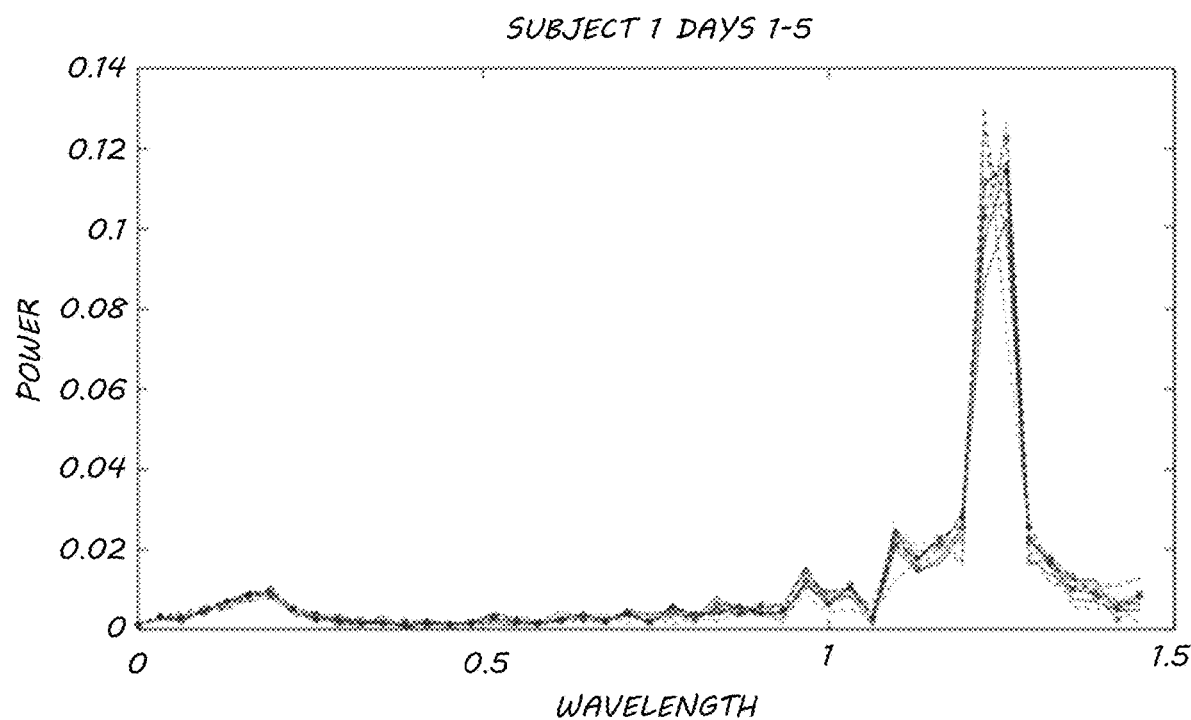
FIG. 19 is a graph of the time invariant data of FIG. 18.

When gathering subject data to determine the unique biometric signature of the subject, the process begins by first performing background subtraction (block 106, FIG. 9) on the data in the time domain. The data is then centered and smoothed and the noise components removed (block 104, FIG. 9) to arrive at the graph in FIG. 18. It was noticed that there are time-varying parts of the data, and time-invariant parts of the data. Thus, the time-varying data were filtered out leaving the time-invariant data as shown in FIG. 19.

Subjects measurements are then taken. When testing an embodiment of the invention, measurements were taken at 121 distinct rotations of each of the 79 human test subjects. Additionally, 35 children from ages 4-12 were tested. As can be seen in the graph in FIG. 19, the time invariance measurements can be sustained from multiple times a day, to a full week. The time-invariant features do not change for the time-invariant portion of the data.

Figure 20:
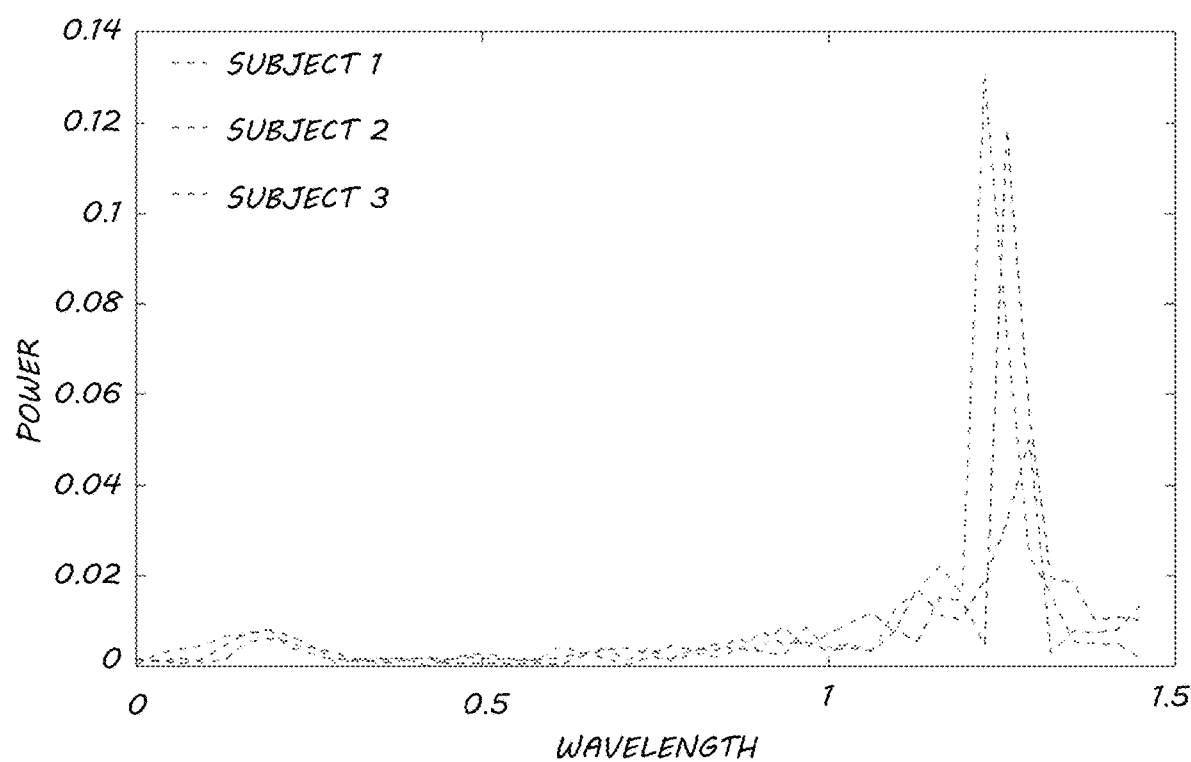
FIG. 20 is a graph of a single feature or a subject vs a different subject in range.

When testing the embodiment of the invention it was also ensured that similar sized individuals had unique individual features. In FIGS. 19 and 20, for each test-subject, and for a single feature, the shape remains consistent over many days and is unique to the subject both in angle and in range.

Figure 21:
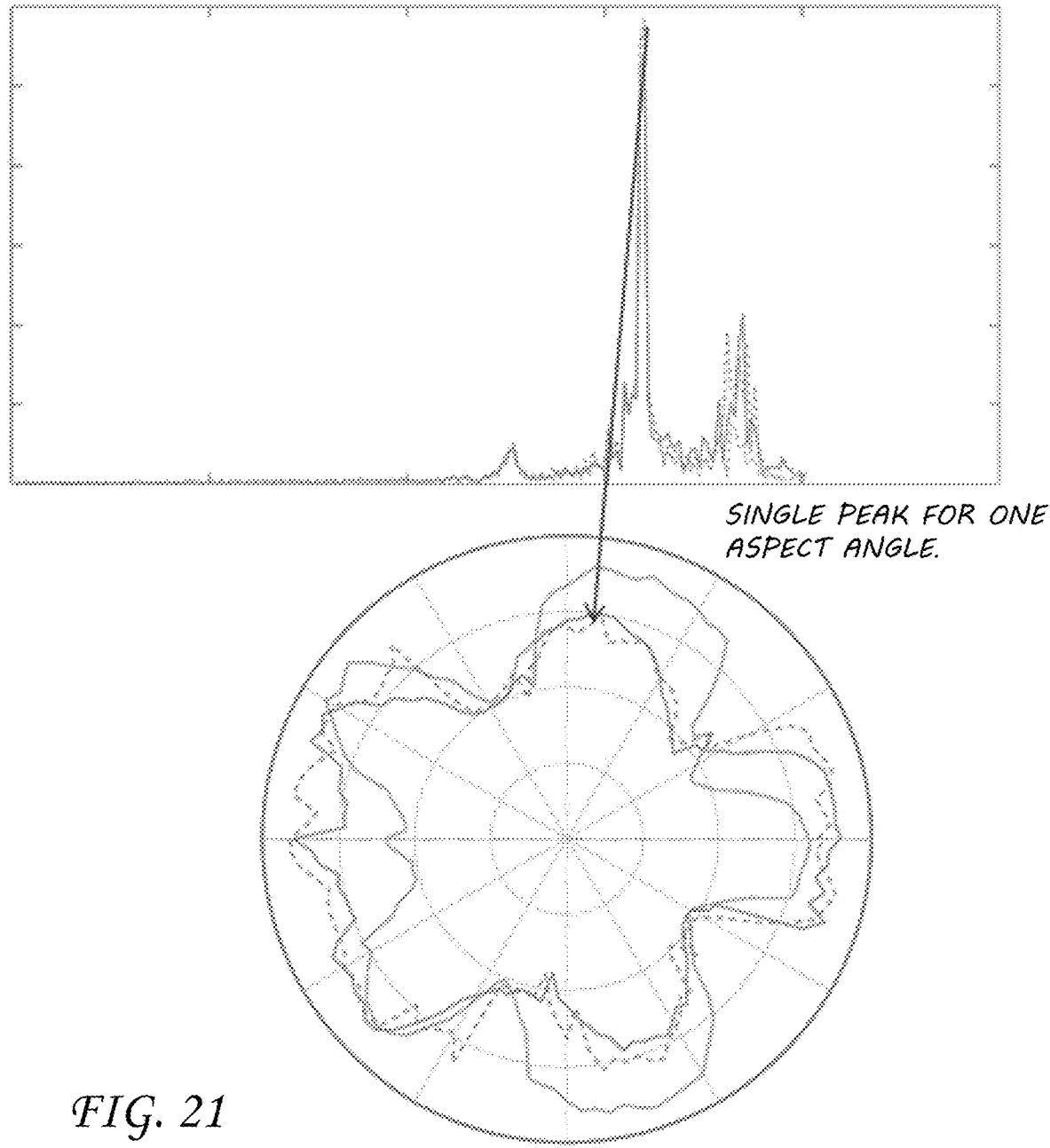
FIG. 21 contains a representation of a polar vs time domain.
Figure 22:
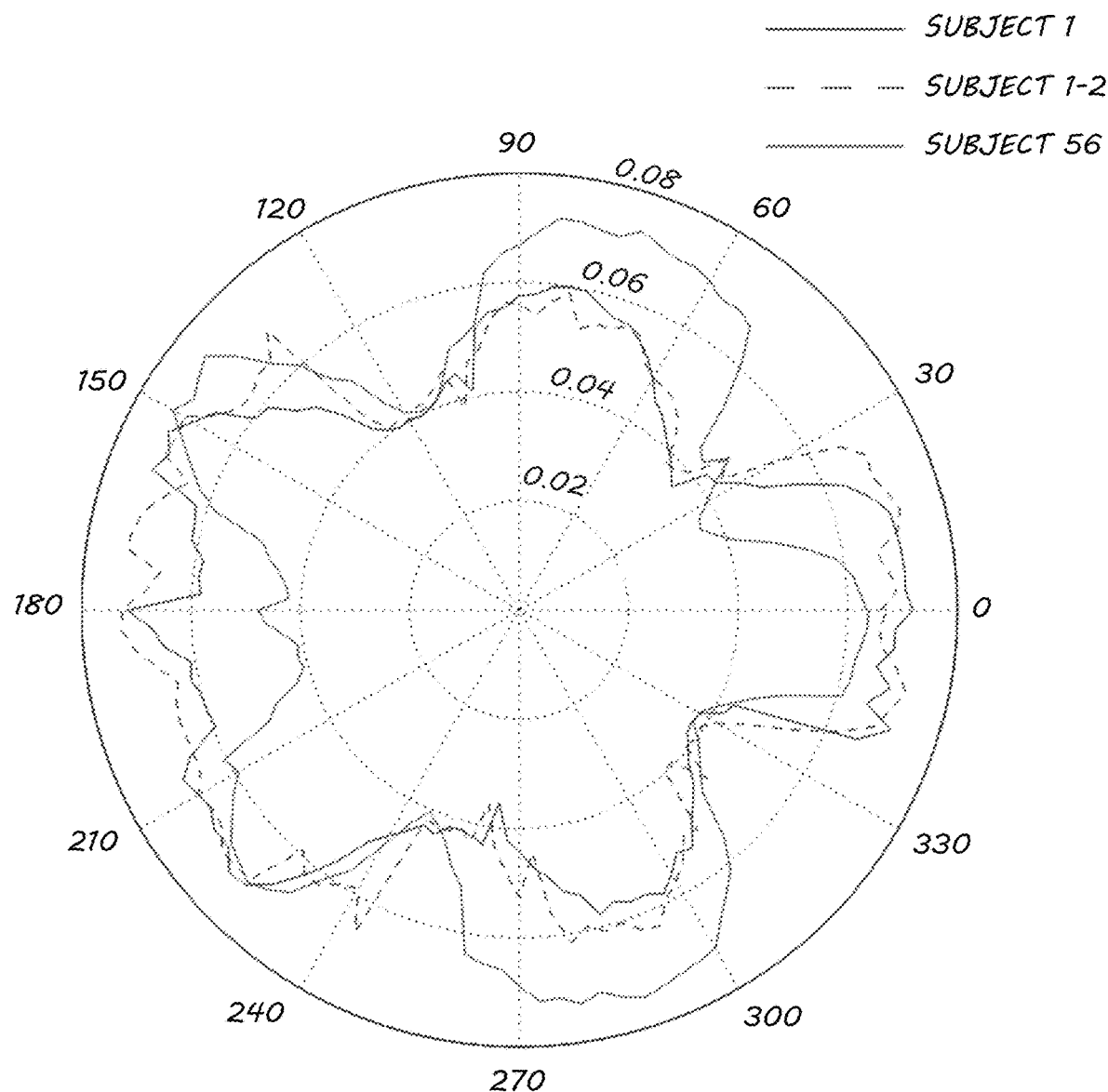
FIG. 22 is a polar plot of a single feature or a subject vs a different subject.

The measurements from the tested embodiment verified that an algorithm for hamming distance calculation that resembles iris detection would work if a unique way were found to create RADAR polar plot of an individual that would serve as the biometric radar signature. The FIGS. 21 and 22 show the unique radar features with the highest likelihood of being a unique biometric radar signature. Much like iris detection methods, the polar-range domain RADAR plots show similar statistical results to that of a biometric iris signature.

Figure 23:
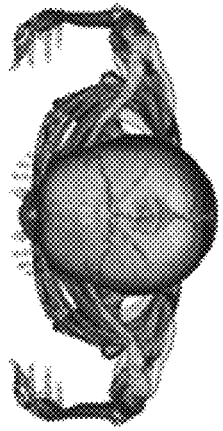
FIG. 23 is a top view of a human skeleton.

FIG. 23 shows the top view of a skeleton. This is the type of image a RADAR operating at high azimuthal (angular) resolution would produce if a plane wave impinges on a subject at zero elevation. In this image, a central axis is recognized with circular or elliptical features that characterize the skull, chest width, and most likely limb features (which was represented in the cylinder model in FIG. 3). This was determined by examination of the anthropometric measurements and prediction of resonant returns and size features of the subjects using the mathematical model in Eq. 1.

Figure 24:
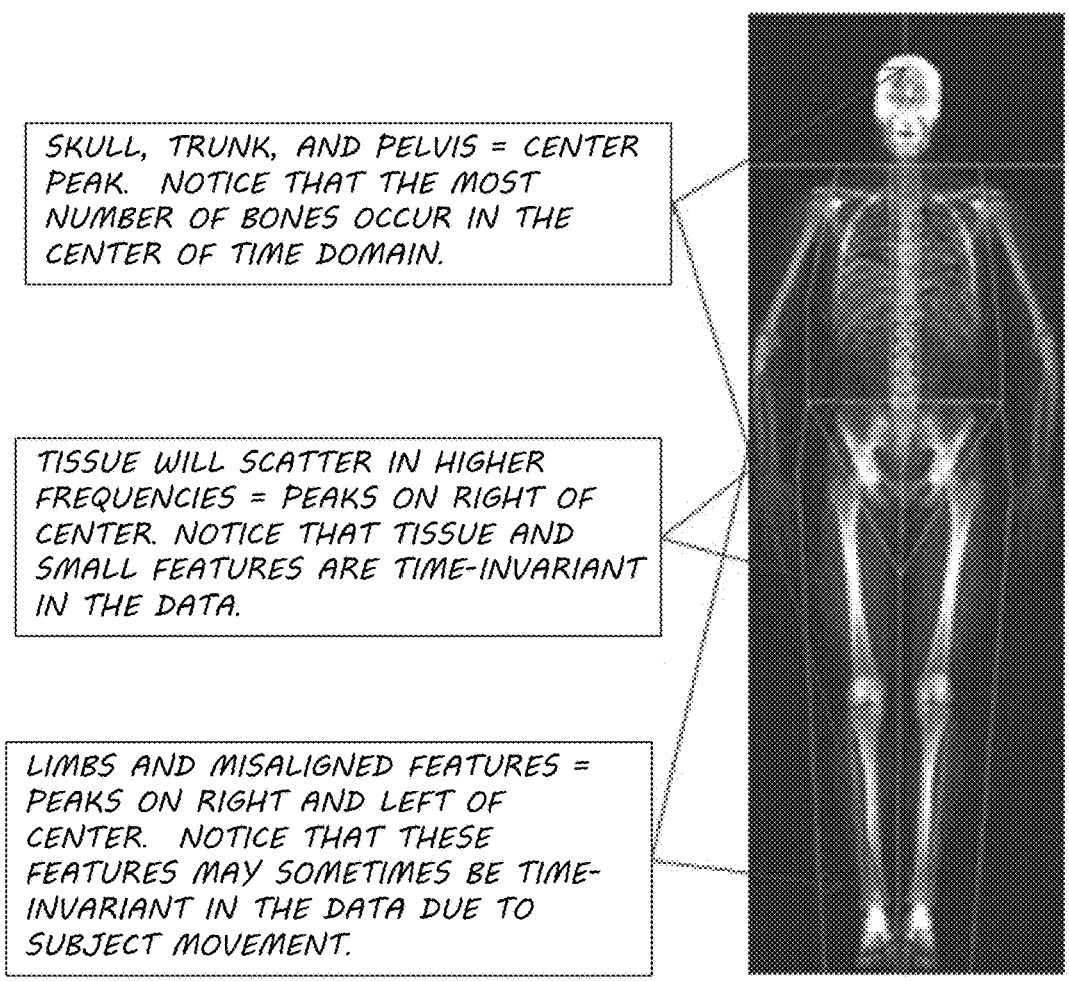
FIG. 24 illustrates alignment of biometric features.

After radar I/Q data is collected from a subject for at least 121 views for the template frequencies, a biometric radar signature may be plotted and matched to the template polar plot. While 121 views are used for this exemplary embodiment, other numbers of views may also be used for other embodiments of the invention. To create an original polar plot, a homotopy (path-finding) method is applied. Each feature will be associated with a view angle, a frequency and a range estimate. The view angle represents a fixed position in the human body that needs to be associated with the radar power spectral density measurement as illustrated in FIG. 24.

As with a picture of a person's face taken by a camera, there are view angles where the camera captures two eyes. Depending on the curvature of the person's face, there could be a span between 3 pi/4 and pi/4 radians that the face can turn and the camera will still capture person's two eyes. Accordingly, there are also view angles where the camera only captures a single eye. If additional information is provided, such as a: the distance between two eyes measured from the picture pixel and b: the distance between two eyes measured in real life, then the perceived focal length (F) can be determined by knowing c: a single fixed distance from the camera to the face. Then F=(b×c)/a. By knowing F, the camera may be moved closer to the face or further from the face (along a straight line) and this new distance between the face and the camera (c') can be determined by using the law of similar triangles to arrive at the formula c'=(a×F)/b.

Figure 25A:
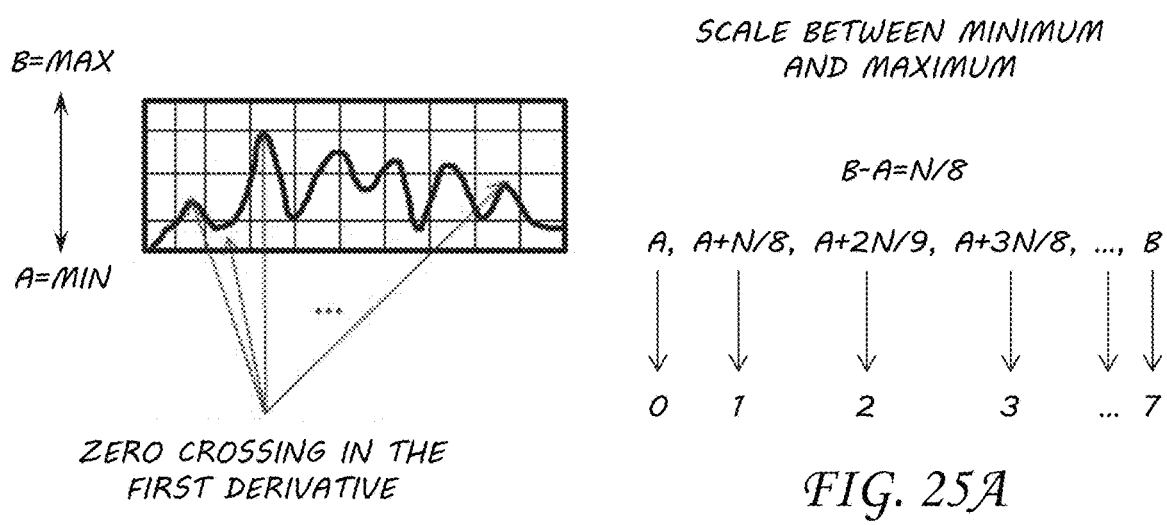
FIGS. 25A-25C illustrate transformation from time-domain radar data into both first and second derivatives.
Figure 25B:
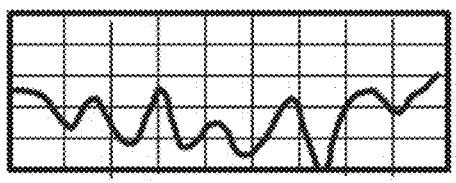
Figure 25C:
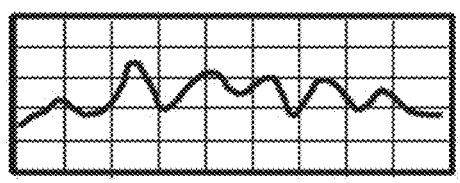

The radar biometric signature associated with the embodiments of the invention is much more complicated than this simple example but is made easier by finding an osculating circle of each view angle. Because sufficient information about the human body is known, the mathematical model in Eq. 1 may be used, which is parametrized by two features, a and b, from each canonical shape that is associated with a human body part, to determine the best frequencies and angles to use to record the template biometric radar signature. By using tabular complex-valued calculus, numerical derivative functions were determined. The data is characterized by spanning 2 derivatives as illustrated in FIGS. 25A-25C. This will achieve two things: 1. Smooth the curve so it does not have so many ridges, and 2. Determine the curvature that would ensure stability of the result when comparing between two subject's scans. See FIGS. 20 and 22.

A resulting data cube would then contain the original data, a first-order correction, and a second order correction. This 121 by 3 matrix (associated to a single frequency) would then be bio-coded using the features determined to be unique via anthropometric and dosimetry studies. These specific features were found in the radar data by careful analysis, Fourier theory and machine learning methods, which are illustrated by FIG. 21. See also FIG. 26. Once the biometric radar signature features were determined, a template polar plot (or key) biometric radar signature can be created. Each subject's template polar plot (or key) biometric radar signature is saved.

This single vector data was filtered using a uniquely designed Gabor-type filter that removes the data that was determined to be strictly noise or clutter. This filter depends on the noise and clutter for the room. A principle component analysis (PCA) method was used to standardize and normalize the data from all subjects. The principle component analysis method considers the following parameters: frequency, time-delay, range, angle, dosimetry-based frequency-depth penetration, physical anthropometry, wavefront-based power spectral density, and scattering function (incident). Each subject, given their own unique parameter values, would have a unique result though the plots will look similar since all humans have similar shapes. The following equations are used for Biometric Authentication Signature (BAS):

$$E(f) = I(f) + iQ(f) \quad (18)$$

$$E(f,\theta) = I(f,\theta) + iQ(f,\theta) \quad (19)$$

$$E(t,\theta) = \int E(f,\theta) e^{2\pi i t f} df \quad (20)$$

$$P(f,\theta) = 10 * \log 10(|E(f,\theta)|^2) \quad (21)$$

$$I_n(t,\theta) = |E(t,\theta)|^2 \quad (22)$$

Figure 26:
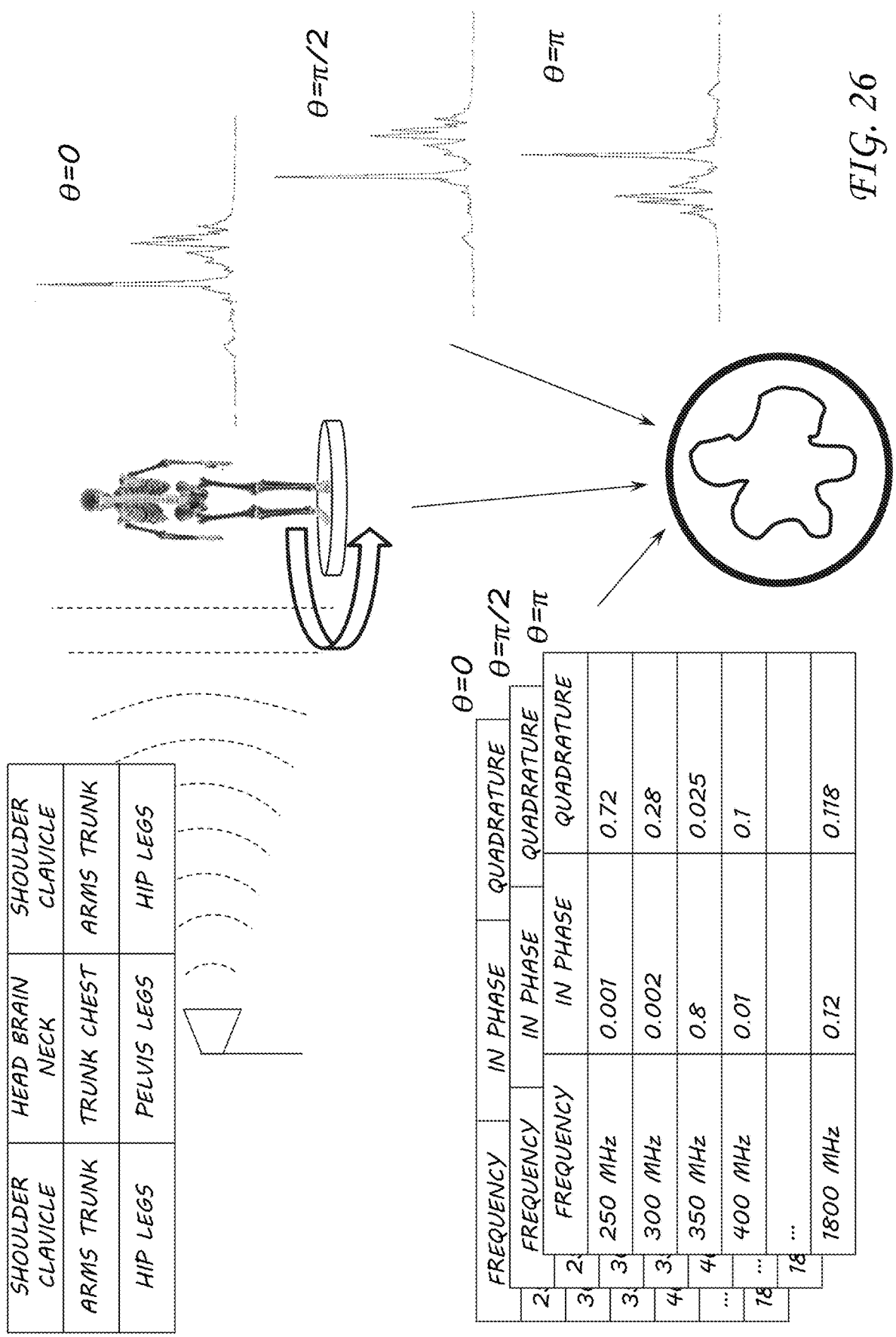
FIG. 26 illustrates a full data representation to generate a polar plot of biometric features.

The unique BAS is determined using the above equations (18)-(22) along with the algorithms in FIGS. 27A-C. Specifically, the tables at the bottom left of FIG. 26 are associated with Eq. 18 [In-phase (I) and Quadrature (Q) as a function of frequency] and Eq. 19 [In-Phase (I) and Quadrature (Q) as a function of frequency and $\theta$]. The graphs illustrated on the right portion of FIG. 26 are associated with Eq. 22 [Intensity as a function of time-delay (range) and $\theta$]. FIGS. 25A-C and 27B are associated with Table 5: Tabular first and second derivative test associated with Intensity ($I_n$) function. Finally, the algorithm in FIG. 27C utilizes all of the equations (18)-(22) including the Fourier Transformed In-Phase and Quadrature as a function of time and $\theta$ in Eq. (20) and Power Spectral Density as a function of frequency and $\theta$ in Eq. (21). Further, a version of the resolution cells, similar to those in Table 2, but as associated with Intensity peaks ($I_n$) in Table 4 and derivative tests in Table 5.

TABLE 4

Resolution Cell (RC) associated with Intensity ($I_n$) peaks

| RC (min) | RC (max) | peak |
|---|---|---|
| 0 | 0.0314 | $x_1$ |
| 0.0314 | 0.0628 | $x_2$ |
| 0.0628 | 0.0942 | $x_3$ |
| 0.0942 | 0.1256 | $x_4$ |
| 0.1256 | 0.157 | $x_5$ |
| 0.157 | 0.1884 | $x_6$ |
| 0.1884 | 0.2198 | $x_7$ |
| 0.2198 | 0.2512 | $x_8$ |
| 0.2512 | 0.2826 | $x_9$ |
| 0.2826 | 0.314 | $x_{10}$ |

TABLE 5

Tabular first and second derivative test associated with Intensity ($I_n$) function

| Interval | 0 < xt1 < x1 | ... | X9 < xt10 < x10 |
|---|---|---|---|
| $I_n'$ | sign($I_n'(x_{t1})$) | ... | sign($I_n'((x_{t10})$)) |
| $I_n''$ | $I_n''(x_{t1})$ | ... | $I_n''(x_{t10})$ |

Because we have an original data set that is 1026 (frequencies)×121 (angles)×3 (derivative test)×2 (I/Q)×10 (RC)×9 (body regions)=67038840~6.7×10$^7$ data points, selecting the unique BAS plot 121×1 is highly unique. To understand why this plot is unique requires using the combinatorics with repetition formula:

$$\binom{r+n-1}{r} = \frac{(r+n-1)!}{r!(n-1)!} \quad (23)$$

where n is the number of things to choose from, and r are chosen, repetition allowed, order doesn't matter. The n of the problem is the number of data points, or n=6.7×10$^7$. The r of the problem is the number of view angles, or r=121. The factorial formula (n)!=n*(n−1)*(n−2) . . . *1, where (0)!=1. The $\binom{a}{b}$ represents the binomial formula. Thus, in our case:

$$\binom{67038840 - 120}{121} = \frac{(67038720)!}{121!(67038839)!} = 1.194497 \times 10^{746}.$$

This suggests that the BAS is highly accurate. The process to match the template plot BAS and the daily compare BAS was developed to compare two vectors associated to different subjects or the same subject measured on different days as illustrated in the comparison algorithm in FIG. 27C.

The algorithm suite should naturally penalize the comparison of two data sets if the features are not consistent.

Note that the template measurement vector will have a prime symbol associated with the subscript. Also note that each algorithm only denotes a single angle measurement. The data matrix is associated with all angle measurements are collected using an externally-controlled turntable. Sample Pre-Processing, Signal Conditioning, and Comparison algorithms are presented in FIGS. 27A-27C.

A confusion matrix, and its associated hamming distance, is determined by comparing all subjects against each other. The confusion matrix determines how many false positives, false negatives, true matches and true rejections. The initial decision value vs. the known decision value were used to determine the confusion matrix. Embodiments of the invention had significantly more successes than failures. Because the illustrated embodiment did not use a binary codification of the data, the hamming distance is not normalized. Once the results are normalized, embodiments of the invention are expected to have a hamming distance value of 0.85 or greater.

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the scope of the general inventive concept.

What is claimed is:

1. A wideband RADAR system for biometric identification and authentication of a human subject, the system comprising:
   a source of wideband RADAR signals;
   an amplifier;
   a splitter in electrical communication with the source of wideband RADAR signals and configured to split a generated signal into a transmit signal and a reference transmit signal;
   a transmitting antenna configured to transmit the transmit signal from the splitter;
   a turntable configured to rotate the human subject;
   a receiving antenna configured to receive transmitted signals reflected from the human subject; and
   a controller configured to process the received reflected signals and generate a resolution cell and polar representations of biometric radar signature features.

2. The wideband RADAR system of claim 1, further comprising:
   a vector network analyzer,
   wherein the vector network analyzer is connected between the receiving antenna and the controller.

3. The wideband RADAR system of claim 1, wherein the receiving antenna is a TEM receiving antenna.

4. The wideband RADAR system of claim 1, wherein the transmitting antenna is a IRA-3Q transmitting antenna.

5. The wideband RADAR system of claim 1, wherein the controller is further configured to:
   pre-process received reflected signals by:
      removing noise from the reflected signals;
      removing background from the reflected signals; and
      removing an antenna response from the reflected signals.

6. The wideband RADAR system of claim 5, wherein the controller is further configured to:
   condition the pre-processed reflected signals.

7. The wideband RADAR system of claim 6, where the pre-processed reflected signals are conditioned by:
   performing first and second numerical derivative tests;
   determining peak locations with an average value filter; and
   determining a peak measurement vector.

8. The wideband RADAR system of claim 1, wherein the controller is further configured to:
   compare the polar representations of biometric radar signature features to a known human subject.

9. The wideband RADAR system of claim 1, wherein the source of wideband RADAR signals comprises an Arbitrary Waveform Generator.

10. The wideband RADAR system of claim 1, wherein the turntable is configured to rotate through a set number of equi-spaced degree measurements.

11. The wideband RADAR system of claim 10, wherein the turntable is configured to rotate through 121 equi-spaced degree measurements.

12. A method of biometric identification and authentication of a human subject from wideband RADAR, the method comprising:
   receiving I/Q wideband RADAR data for a subject for at least 121 views;
   preprocessing the received data by:
      centering the received data;
      removing noise from the received data using a modified Gabor filter; and
      removing background from the received data;
   forming a data cube by processing the preprocessed received data by:
      performing first and second numerical derivative tests;
      determining peak locations; and
      determining a peak measurement vector;
   determining biometric radar signatures by bio-coding the data cube using features determined to be unique via anthropometric and dosimetry studies;
   generating a template polar plot biometric radar signature;
   retrieving a saved subject template; and
   comparing the template polar plot biometric radar signature to the saved subject template.

* * * * *